(12) United States Patent
Knox et al.

(10) Patent No.: US 11,571,336 B2
(45) Date of Patent: Feb. 7, 2023

(54) REFRACTIVE INDEX SHAPING LASER WRITING PROCESS CONTROL

(71) Applicant: University of Rochester, Rochester, NY (US)

(72) Inventors: Wayne Knox, Rochester, NY (US); Jonathan D. Ellis, Tucson, AZ (US); Krystel R. Huxlin, Rush, NY (US); Daniel R. Brooks, Rochester, NY (US); Kaitlin T. Wozniak, Rochester, NY (US)

(73) Assignee: University of Rochester, Rochester, NY (US)

( * ) Notice: Subject to any disclaimer, the term of this patent is extended or adjusted under 35 U.S.C. 154(b) by 52 days.

(21) Appl. No.: 16/964,477

(22) PCT Filed: Jan. 25, 2019

(86) PCT No.: PCT/US2019/015173
§ 371 (c)(1),
(2) Date: Jul. 23, 2020

(87) PCT Pub. No.: WO2019/147952
PCT Pub. Date: Aug. 1, 2019

(65) Prior Publication Data
US 2021/0052425 A1    Feb. 25, 2021

Related U.S. Application Data

(60) Provisional application No. 62/622,473, filed on Jan. 26, 2018.

(51) Int. Cl.
*A61F 9/008* (2006.01)
(52) U.S. Cl.
CPC ...... *A61F 9/00827* (2013.01); *A61F 9/00804* (2013.01); *A61F 2009/00855* (2013.01); *A61F 2009/00897* (2013.01)

(58) Field of Classification Search
CPC ........ A61F 9/00827; A61F 2009/00804; A61F 2009/00855; A61F 2009/00897
See application file for complete search history.

(56) References Cited

U.S. PATENT DOCUMENTS 7,789,910 B2    9/2010    Knox et al.
8,337,553 B2    12/2012   Knox et al.
(Continued)

OTHER PUBLICATIONS

European Patent Office (ISA/EP), International Search Report and Written Opinion from International Patent Application No. PCT/US2019/015173, as completed Jun. 17, 2019.
(Continued)

*Primary Examiner* — Nathan J Jenness
*Assistant Examiner* — Skylar Lindsey Christianson
(74) *Attorney, Agent, or Firm* — Andrew J. Anderson, Esq.; Harter Secrest & Emery LLP

(57) ABSTRACT

Refractive index writing system and methods employing a pulsed laser source for providing a pulsed laser output at a first wavelength; an objective lens for focusing the pulsed laser output to a focal spot in an optical material; a scanner for relatively moving the focal spot with respect to the optical material at a relative speed and direction along a scan region for writing one or more traces in the optical material defined by a change in refractive index; and a controller for controlling laser exposures along the one or more traces in accordance with a calibration function for the optical material to achieve a desired refractive index profile in the optical material. The refractive index writing system may be for writing traces in in vivo optical tissue, and the controller may be configured with a calibration function obtained by calibrating refractive index change induced in enucleated ocular globes. A real-time process control monitor for detecting emissions from the optical material transmitted (Continued)

through the objective lens at a second wavelength may further be employed while writing the one or more traces.

19 Claims, 13 Drawing Sheets

(56) References Cited

U.S. PATENT DOCUMENTS

| | | | |
|---|---|---|---|
| 8,486,055 B2 | 7/2013 | Knox et al. | |
| 8,512,320 B1 | 8/2013 | Knox et al. | |
| 8,617,147 B2 | 12/2013 | Knox et al. | |
| 2012/0310223 A1* | 12/2012 | Knox | A61F 9/00827 606/5 |
| 2012/0310340 A1† | 12/2012 | Knox et al. | |
| 2013/0226162 A1 | 8/2013 | Knox et al. | |
| 2013/0268072 A1 | 10/2013 | Smith et al. | |
| 2015/0126979 A1 | 5/2015 | Knox et al. | |
| 2016/0144580 A1* | 5/2016 | Knox | G02B 26/10 606/4 |

OTHER PUBLICATIONS

Gandara-Montano et al., "Femtosecond laser writing of freeform gradient index microlenses in hydrogel-based contact lenses", Optical Materials Express, vol. 5, No. 10, DOI: 10.1364/OME.5.002257, p. 2257, XP055573679, Sep. 22, 2015.

Valeria Nuzzo et al., "In situ monitoring of second-harmonic generation in human corneas to compensate for femtosecond laser pulse attenuation in keratoplasty", Journal of Biomedical Optics 12(6), 064032, Nov./Dec. 2007.

Liping Cui et al., "High-Resolution, noninvasive, Two-Photon Fluorescence Measurement of Molecular Concentrations in Corneal Tissue", Investigative Ophthalmology & Visual Science, Apr. 2011, vol. 52, No. 5, pp. 2556-2564, Copyright 2011, The Association for Research in Vision and Ophthalmology, Inc.

\* cited by examiner
† cited by third party

REFRACTIVE INDEX SHAPING LASER WRITING PROCESS CONTROL

GOVERNMENT SUPPORT CLAUSE

This invention was made with Government Support under EY015836 and EY001319 awarded by the National Institutes of Health and IIP1549700 and IIP1738506 awarded by the National Science Foundation. The Government has certain rights in the invention.

TECHNICAL FIELD

The application relates to using a pulsed laser to modify the refractive index of an optical medium, and particularly to a control monitoring system for laser writing refractive index changes into ocular tissues or replacement or augmentative structures made of optical polymeric materials to modify or enhance the visual performance of patients, and methods for calibrating refractive index change induced in ocular tissue by femtosecond laser writing as a function of laser exposure.

BACKGROUND OF THE INVENTION

Pulsed lasers operating within specified regimes specially adapted to target optical materials have been demonstrated to produce localized refractive index changes in the optical materials without otherwise damaging the materials in ways that would impair vision. The energy regimes, while above the nonlinear absorption threshold, are maintained below the breakdown thresholds of the optical materials at which significant light scattering or absorption degrades their intended performance. The considerations of these adapted energy regimes include pulse wavelength, pulse energy, pulse duration, the size and shape into which the pulses are focused into the optical material, and the temporal and physical spacing of the pulses. Such process may be referred to as Intra-tissue Refractive Index Shaping (IRIS) in biological tissues or Intra-Polymer Refractive Index Shaping (IRIS) in optical polymers, such as intraocular lenses, contact lenses or corneal inlays.

Examples include US Patent Application Publication No. 2013/0226162 entitled Method for Modifying the Refractive Index of Ocular Tissues, which discloses a laser system for changing the index of refraction of cornea tissue in a living eye for forming of modifying optical elements including Bragg gratings, microlens arrays, zone plates, Fresnel lenses, and combinations thereof. US Patent Application Publication No. 2013/0268072 entitled Optical Hydrogel Material with Photosensitizer and Method for Modifying the Refractive Index discloses a method for modifying the refractive index of an optical, hydrogel polymeric material prepared with a photosensitizer particularly for the purposes of enhancing the efficiency of nonlinear absorption and increasing the scan rate at which refractive structure can be formed. US Patent Application Publication No. 2015/0126979 entitled Method for Modifying the Refractive Index of an Optical Material discloses the writing of selected regions of optical hydrogel materials prepared with a hydrophilic monomer following implantation of the prepared material into the eye of the patient. U.S. Publication No. 2012/0310340 describes a method for providing changes in refractive power of an optical device made of an optical, polymeric material by forming at least one laser-modified, gradient index (GRIN) layer disposed between an anterior surface and a posterior surface of the device by scanning with light pulses from a visible or near-IR laser along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned. U.S. Publication 2012/0310223 discloses a method of modifying the refractive index in ocular tissues wherein a laser-modified gradient index (GRIN) layer is formed directly in at least one of the corneal stroma and the crystalline lens. These referenced patent applications are hereby incorporated by reference, particularly as examples for writing refractive structures in optical materials, and as representative background technologies subject to the improvements set forth herein.

In such processes, the irradiated regions of the optical tissue or optical polymeric material can take the form of two- or three-dimensional, area or volume filled refractive structures. The refractive structures are formed by scanning the laser over a select region of the optical tissue or polymeric material resulting in refractive optical structures that can provide spherical, aspherical, toroidal, or cylindrical correction to the optical tissue or a polymeric lens. In fact, any optical structure can be formed to yield positive or negative power corrections. Moreover, the optical structures can be stacked vertically or written in separate planes in optical tissue or the polymeric material to act as a single lens element.

The control of such laser writing process in which refractive index changes can be written into optical materials while avoiding damage to the materials remains of importance whether the optical materials are of living origin or man-made, and whether the optical materials are positioned in vivo or in vitro, but is of particular significance for in vivo processes. Improved processes and systems for monitoring the delivery of concentrated pulse energies of a laser beam in a form that achieves the desired refractive index changes in the optical materials without exceeding the damage threshold at which the desired optical performance is degraded are desirable.

SUMMARY

An embodiment as disclosed is directed towards a refractive index writing system comprising: a pulsed laser source for providing a pulsed laser output at a first wavelength; an objective lens for focusing the pulsed laser output to a focal spot in an optical material; a scanner for relatively moving the focal spot with respect to the optical material at a relative speed and direction along a scan region for writing one or more traces in the optical material defined by a change in refractive index; and a controller for controlling laser exposures along the one or more traces in accordance with a calibration function for the optical material to achieve a desired refractive index profile in the optical material by varying the laser power and/or relative scan speed for maintaining an energy profile within the optical material along the scan region above a nonlinear absorption threshold of the optical material and below a breakdown threshold of the optical material at which significant light scattering or absorption degrades the intended performance of the optical material; wherein the refractive index writing system is for writing traces in in vivo optical tissue, and the controller is configured with a calibration function obtained by calibrating refractive index change induced in test ocular tissue by femtosecond laser writing as a function of laser exposure by:

writing test patterns in sections of one or more enucleated ocular globes with a femtosecond laser at different laser exposures for different sections of the test patterns; and determining the induced refractive index change in the written patterns relative to unmodified tissue in areas surrounding the written patterns as a function of the laser exposure from interferograms taken of the written patterns and surrounding areas in their natural curved orientation.

A further embodiment as disclosed is directed towards a method of writing localized refractive index changes in optical materials with a pulsed laser source providing a pulsed laser output at a first wavelength within energy regimes above a nonlinear absorption threshold of the optical materials and below a breakdown threshold of the optical materials at which significant light scattering or absorption degrades their intended performance, comprising steps of: producing a collimated output beam composed of a succession of pulses having a pulse energy between 0.01 nJ and 10 nJ, a pulse duration between 8 fs and 500 fs, and a repetition rate between 10 MHz and 500 MHz; focusing the beam with an objective lens to a focal spot within the optical material; relatively moving the objective lens with respect to the optical material at a relative speed and relative direction to write one or more traces defined by a change in refractive index of the optical material; and controlling laser exposures along the one or more traces in accordance with a calibration function for the optical material to achieve a desired refractive index profile in the optical material by varying the laser power and/or relative scan speed to maintain an energy profile within the optical material along the scan region above a nonlinear absorption threshold of the optical material and below a breakdown threshold of the optical material at which significant light scattering or absorption degrades the intended performance of the optical material; wherein the optical material is in vivo optical tissue, and further comprising wherein the calibration function for the optical material is obtained by calibrating refractive index change induced in test ocular tissue by femtosecond laser writing as a function of laser exposure by: writing test patterns in sections of one or more enucleated ocular globes with a femtosecond laser at different laser exposures for different sections of the test patterns; and determining the induced refractive index change in the written patterns relative to unmodified tissue in areas surrounding the written patterns as a function of the laser exposure from interferograms taken of the written patterns and surrounding areas in their natural curved orientation.

A further embodiment as disclosed is directed towards a refractive index writing system comprising: a pulsed laser source for providing a pulsed laser output at a first wavelength; an objective lens for focusing the pulsed laser output to a focal spot in an optical material; a scanner for relatively moving the focal spot with respect to the optical material at a relative speed and direction along a scan region for writing one or more traces in the optical material defined by a change in refractive index; a real-time process control monitor for detecting emissions from the optical material transmitted through the objective lens at a second wavelength while writing the one or more traces, comprising a photodetector, a lens for focusing the emissions transmitted through the objective lens onto the photodetector, and a filter for passing emissions at the second wavelength to the detector and blocking back-reflected pulse laser light of the first wavelength from the photodetector; and a controller for controlling laser exposures along the one or more traces in accordance with a calibration function for the optical material to achieve a desired refractive index profile in the optical material by varying the laser power and/or relative scan speed for maintaining an energy profile within the optical material along the scan region above a nonlinear absorption threshold of the optical material and below a breakdown threshold of the optical material at which significant light scattering or absorption degrades the intended performance of the optical material, and for further controlling the laser exposure in response to an emission from the optical material at the second wavelength detected by the real-time process control monitor.

A further embodiment as disclosed is directed towards a method of writing localized refractive index changes in optical materials with a pulsed laser source providing a pulsed laser output at a first wavelength within energy regimes above a nonlinear absorption threshold of the optical materials and below a breakdown threshold of the optical materials at which significant light scattering or absorption degrades their intended performance, comprising steps of: producing a collimated output beam composed of a succession of pulses having a pulse energy between 0.01 nJ and 10 nJ, a pulse duration between 8 fs and 500 fs, and a repetition rate between 10 MHz and 500 MHz; focusing the beam with an objective lens to a focal spot within the optical material; relatively moving the objective lens with respect to the optical material at a relative speed and relative direction to write one or more traces defined by a change in refractive index of the optical material; detecting emissions from the optical material transmitted through the objective lens at a second wavelength while writing the one or more traces by focusing the emissions transmitted through the objective lens onto a photodetector and blocking back-reflected pulse laser light of the first wavelength from the photodetector; and controlling laser exposures along the one or more traces in accordance with a calibration function for the optical material to achieve a desired refractive index profile in the optical material by varying the laser power and/or relative scan speed to maintain an energy profile within the optical material along the scan region above a nonlinear absorption threshold of the optical material and below a breakdown threshold of the optical material at which significant light scattering or absorption degrades the intended performance of the optical material, and further controlling the laser exposure in response to a detected emission from the optical material at the second wavelength.

A further embodiment as disclosed is directed towards a method for calibrating refractive index change induced in ocular tissue by femtosecond laser writing as a function of laser exposure, comprising: writing test patterns in sections of one or more enucleated ocular globes with a femtosecond laser at different laser exposures for different sections of the test patterns; dissecting the sections having test patterns written in them and surrounding areas from the enucleated globes; mounting the dissected portions into a wetcell with the portions placed in their natural curved orientation in the wetcell; and determining the induced refractive index change in the written patterns relative to unmodified tissue in the portions as a function of the laser exposure from interferograms taken of the mounted dissected portion with an interferometer. The test patters may be written in such embodiment with a femtosecond laser at different laser exposures for different sections of the test patterns by varying the laser power and/or laser scan rate, e.g., at different laser powers and constant scan rate for different sections of the test patterns, and/or at different laser scan rates and constant power for different sections of the test patterns.

Further specific embodiments of the disclosure include those set forth in the appended claims, and as described in the specification.

In various embodiments the writing systems and methods may be for writing refractive index structures in optical polymeric materials or ocular tissues. In specific embodiments the writing systems and methods may be for writing refractive index structures in corneal optical tissue. The refractive index changes written into the optical material include relatively increasing or decreasing the refractive index of the scanned regions of the optical material according to the local reaction of the optical material to the pulses delivered.

In the various embodiments of the disclosure, one or more of the following features may be employed alone or in combination: the focused, pulse laser output may have a pulse energy from 0.01 nJ to 10 nJ; the pulsed laser output may be in the visible or near-IR spectrum; a multiple-photon-absorbing chromophore may be applied to the optical polymeric materials or ocular tissue prior to modifying the refractive index of the optical polymeric materials or ocular tissue; the multiple-photon-absorbing chromophore comprises a two-photon-absorbing chromophore; the ocular tissue comprises tissue of a lens; the ocular tissue comprises tissue of a cornea; locations defined by the focus spot are selected to form a structure selected from the group consisting of Bragg gratings, arbitrary wavefronts, microlens arrays, zone plates, and Fresnel lenses; the laser pulses are emitted at a frequency between 1 MHz and 10 GHz; the laser pulse frequency is between 10 MHz and 500 MHz; the pulse width is between 8 fs and 1000 fs; the pulse width is between 10 fs and 500 fs; the pulse width is between 10 fs and 100 fs; the laser pulses have an average power between 1 mW and 20 W; the laser pulses have an average power between 1 mW and 1,000 mW; the laser pulses have a pulse energy between 0.01 nJ and 10 nJ; the laser pulses have a pulse energy between 0.1 and 2 nJ; the size of the focus spot is between 0.5 micrometer and 2 micrometer; the focus spot is scanned at a scanning speed between 0.1 micrometer/s and 10 m/s; the focus spot is scanned at a scanning speed of at least 1 mm/s; the focus spot is scanned at a scanning speed of at least 100 mm/s; the focus spot is scanned at a scanning speed of at least 1 m/s; the laser pulses have a wavelength between 350 and 1,300 nm; the laser pulses have a wavelength between 400 and 1,100 nm; the laser pulses have a wavelength between 600 and 1,000 nm; the laser pulses have a wavelength between 700 and 900 nm; the laser pulses have a wavelength between 1,000 and 1,300 nm; the laser pulses have a wavelength between 350 and 600 nm; the laser pulses have a wavelength between 400 and 600 nm; the objective lens has a numerical aperture between 0.28 and 1.0.

BRIEF DESCRIPTION OF THE DRAWING FIGURES

DETAILED DESCRIPTION OF THE INVENTION

In IRIS refractive index writing systems such as described in the references cited in the background section, a pulsed laser source provides a pulsed laser output at a first wavelength, and an objective lens is used to focus the pulsed laser output to a focal spot in an optical material. A scanner is used for relatively moving the focal spot with respect to the optical material at a relative speed and direction along a scan region for writing one or more traces in the optical material defined by a change in refractive index. A controller may be employed for controlling laser exposures along the one or more traces in accordance with a calibration function for the particular optical material to achieve an expected desired refractive index profile in the optical material by varying the laser power and/or relative scan speed for maintaining an energy profile within the optical material along the scan region above a nonlinear absorption threshold of the optical material and below a breakdown threshold of the optical material at which significant light scattering or absorption would be expected to result in the optical material which would damage or degrade the intended performance of the optical material.

Figure 1:
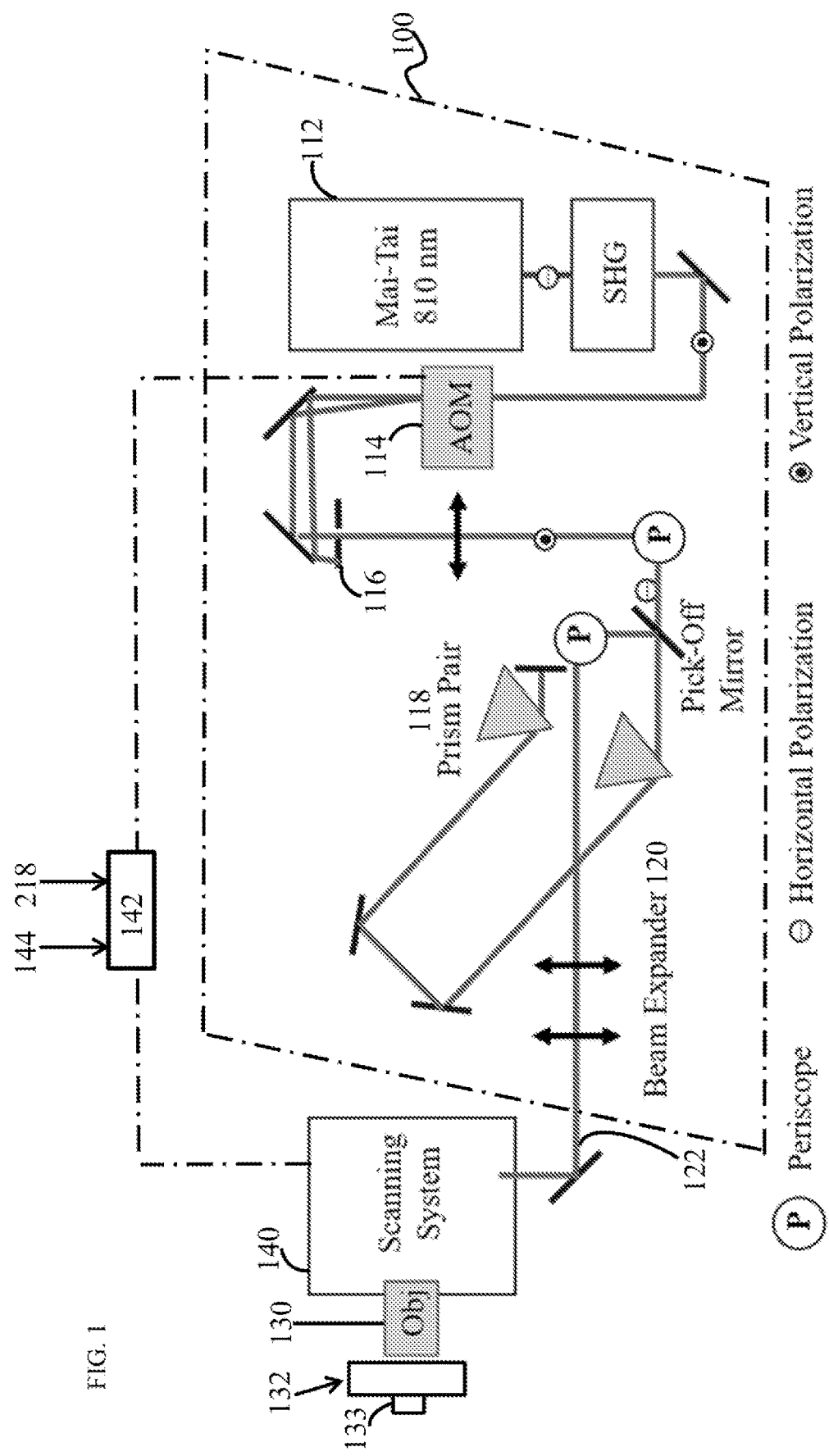
FIG. 1 is a diagram of a laser system that may be used in the present disclosure for writing refractive index structures in an optical material.

An exemplary writing system that may be used for embodiments of the present disclosure is illustrated in FIG. 1. A frequency doubled 810 nm Ti:Sapphire laser 112 operating a wavelength of 405 nm to create bulk optical phase change is directed through an acousto-optic modulator (AOM) 114 in order to enable in process, fast laser power control. The AOM uses an acoustic wave to diffract a portion of the laser light into the $1^{st}$ diffracted order with the amount of diffracted light dependent on the amplitude of the acoustic wave. The $0^{th}$ order, undiffracted light is blocked by an iris 116 and the $1^{st}$ order is used as the beam for the remainder of the system. The light then passes through a pair of prisms 118 to compensate for dispersion, producing a final pulse width of 165 fs. The beam is then directed through a beam expander 120 to enlarge the NA. Components 112-120 together comprise a pulsed laser source 100 which provides a pulsed laser output 122 at a first wavelength to an objective lens 130, which objective lens is used to focus the pulsed laser output to a focal spot in an optical material. Due to thermal bloom in the prisms, the NA is laser power dependent and ranges from 0.55 at higher powers to 0.7 at lower powers. The beam may be steered through a scanning system 140 designed, e.g., around a custom flexure-based scanning head described in Brooks, D. R., et al., *Precision large field scanning system for high numerical aperture lenses and application to femtosecond micromachining of ophthalmic materials*. Review of Scientific Instruments, 2014. 85(6): p. 065107, with objective 130 being an attached water immersion objective which scans the focal region of the objective through optical material being written in, such as a cornea or polymeric material lens. The flexure stage for the referenced scanning system is driven using four voice coil (VC) motors, and enabled stroke lengths of greater than 8 mm along a first scan axis, allowing patterns to be written at greater than 8 mm diameter, which is desirable for patterns written in the cornea or an ophthalmic lens. Further scan stages for scan directions along second and third axes perpendicular to the flexure scan stage direction scan axis may be similar to those described below with respect to the scanner embodiment of FIG. 2, enabling x, y, z axes scan control. Motions along the various axes can be controlled by a controller 142 that translates inputs 144 in the form of desired writing patterns into motions along the various axes as described similarly in the embodiment of FIG. 2.

Controller 142 can also control AOM 114 for regulating the intensity of the pulsed laser output 122 in relation to motions along one or more of the scanner 140 motion axes. For example, the beam intensity at the focal spot can be changed during a scan along the first scan axis, or the beam intensity at the focal spot can be reset to a new fixed value before each new trace along the first scan axis is written, similarly as described in the embodiment of FIG. 2.

An ocular patient interface 132, e.g. comprising a vacuum suction ring 133 as may be conventionally employed in optical surgeries, may further be employed for coupling the writing system to a cornea of a patient.

Figure 2:
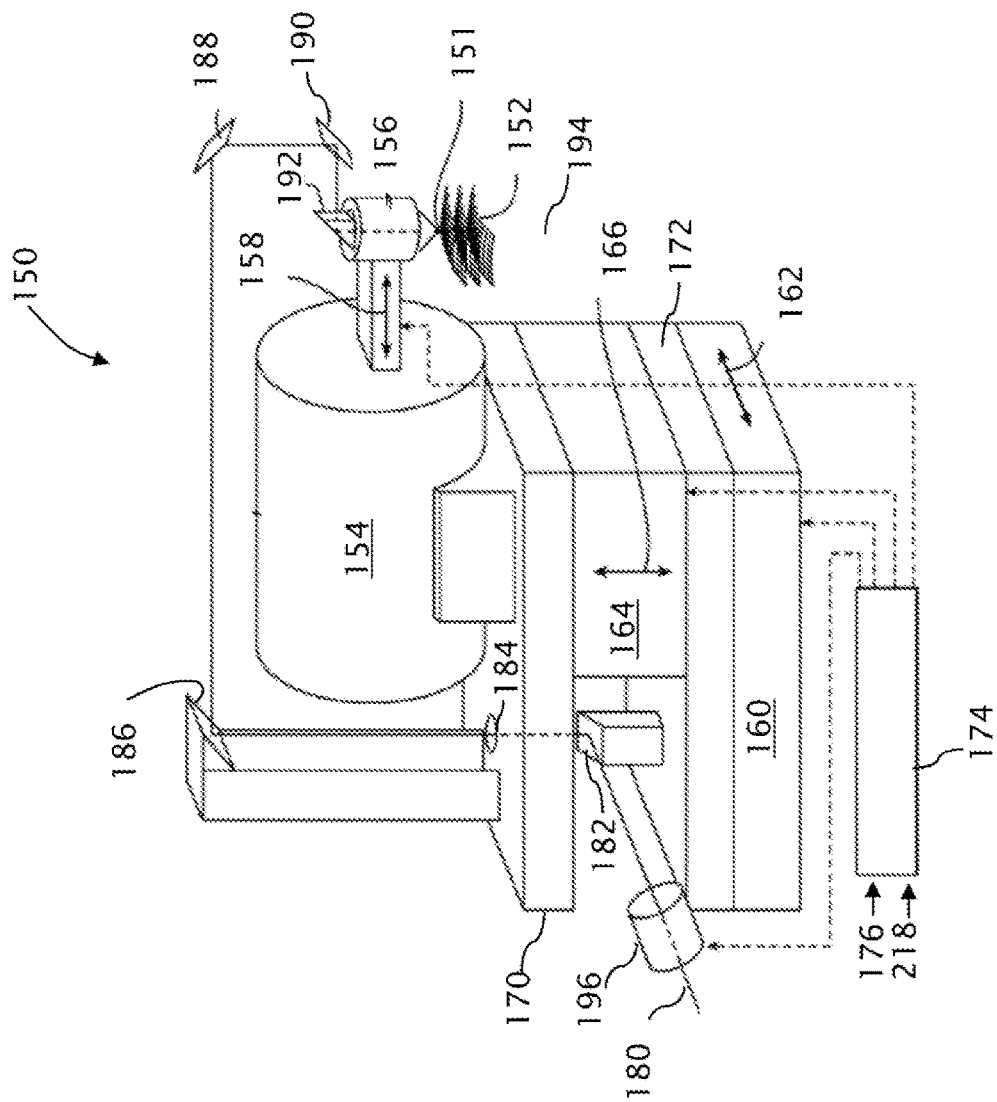
FIG. 2 is a diagram of laser system that may be used in the present disclosure including a specific optomechanical scanner for translating the focal spot along three orthogonal axes for writing refractive index structures in an optical material.

FIG. 2 is a schematic diagram of a further specific type of optomechanical scanner 150 useful in embodiments of the disclosure for writing refractive structures 152 within an optical material with stacked stages to provide for relatively moving a focusing system along three coordinate axes with respect to the optical material. The optomechanical scanner 150 includes a reciprocal shaker (e.g. a rapidly shaking impeller) as a fast axis scanner 154 that provides for rapidly translating an optics assembly 156 along a first scanning motion axis 158. The optics assembly 156 includes an objective lens for focusing working beams into an optical material. A high speed depth control stage and a spherical aberration correction stage can also be incorporated into the optics assembly 156. The high speed depth control can correct for angular motion errors to ensure and the spherical aberration stage can be used to correct for spherical aberrations to improve focal spot quality. A focal spot 151 of the working beam is directed along scan paths in the optical material as imparted by the optomechanical scanner 150.

The optomechanical scanner 150 also includes a motion stage 160 for translating both the optics assembly 156 and the fast axis scanner 154 along a second scanning motion axis 162, which is oriented orthogonal to the first scanning motion axis 158. The motion stage 160 can be arranged to provide continuous or stepped motions in synchronism with the motion imparted by the fast axis scanner 154. A precision height stage 164 is interposed between the motion stage 160 and the fast axis scanner 154 to raise and lower the fast axis scanner along a third scanning motion axis 166 for such purposes as controlling the depth at which the focal spots 151 are written into the optical material.

The optomechanical scanner 150 is particularly arranged for moving the optics assembly 156 with respect to the optical material, which can be particularly useful for in-vivo applications where the optical material cannot be as easily moved. However, for other applications or considerations, the motion axes can be distributed between the optics assembly 156 and the optical material in any combination, and one or more additional motion axes, including rotational axes, can be added as required.

The fast axis scanner 154 can be a commercial vibration exciter to provide high speed reciprocal motion. One example of such a commercial vibration exciter is a Brüel and Kjær Measurement Exciter Type 4810 sold by Brüel & Kjær Sound & Vibration Measurement A/S of Nærum, Denmark. The motion stages 160 and 164 can be a high-precision linear stages, such as model GTS70 for lateral motion and model GTS20V for vertical motion from the Newport GTS Series, sold by Newport Corporation of Irvine, Calif. and adapted via appropriate interface plates 170 and 172 for stacking the motion axes.

Motions along the various axes 158, 162 and 164 can be controlled by an arrangement of controllers and amplifiers 174 that translate inputs 176 in the form of desired writing patterns into motions along the various axes 158, 162, and 164. For example, the fast axis scanner 154 can be controlled by an arbitrary waveform generator. Such waveform generators are sold by Agilent Technologies, Inc. of Santa Clara, Calif. The waveform for the motions along the first scanning motion axis 158 are arranged, for example, to result in the desired refractive index pattern along the first scanning motion axis 158. Instead of sending an arbitrary waveform to the fast axis scanner 154, a specially tuned sine wave can be sent to maximize performance. For example, the drive frequency can be tuned to a resonance frequency of the fast axis scanner 154 to enable high speed motion while inducing minimal disturbances into the supporting structures including the underlying motion stages 160 and 166.

The working beam 180 is aligned and steered along each axis of motion to ensure proper alignment of the working beam 180 with the optics assembly 156. For example a reflector 182 mounted on the interface plate 172 receives the working beams 180 in an orientation aligned with the motion axis 162 and redirects the working beam 180 in the direction of the motion axis 166 through an aperture 184 in the interface plate 170 to a reflector 186 that mounted together with the fast axis scanner 154 on the interface plate 170. The reflector 186 redirects the working beam 180 in the direction of the motion axis 158 above the fast axis scanner 154. Reflectors 188 and 190, which are also preferably mounted from the interface plate 170 redirect the working beams 180 within the same plane to a reflector 192, such as a fold prism, which aligns the working beams 180 with an optical axis 194 of the optics assembly 156.

Other types of single or multi-axis scanners can be employed, such as scanners using angularly scanning rotating polygon mirrors or angularly scanned galvanometer-controlled mirrors with image relaying systems to direct the working beam 180 over appropriate pathways for writing refractive structures 152 within an optical material.

The controllers and amplifiers 174 can also include a second synchronized arbitrary waveform generator for controlling a modulator 196, such as an electro-optic modulator or an acousto-optic modulator, for regulating the intensity of the working beams 180 in relation to motions along one or more of the motion axes 158, 162, and 166. For example, the beam intensity at the focal points 151 can be changed during a scan along the motion axis 158, or the beam intensity at the focal points can be reset to a new fixed value before each new trace is written.

The objective lens 130, 156 can take the form of a microscope objective having a numerical aperture of preferably at least 0.28 but higher numerical apertures of 0.7 through 1.0 are often preferred if sufficient working distance is present. As treatment zone, the focal spot occupies a volume of space within which the power densities of the working beam is sufficient to change the refractive index of the optical material without inducing damage. Positive or negative changes in refractive index can be imparted by the working beam depending upon the reaction of the optical material to the pulses delivered by the beam.

In various embodiments, the laser source employed can more particularly be fashioned as mode-locked Ti:Sapphire laser (e.g., a Spectra-Physics Ti:Sapphire oscillator such as MaiTai-HP available from Spectra-Physics, a Newport company, in Santa Clara, Calif.) pumped by a frequency-doubled Nd:YVO4 laser. The laser can generate, for example, a succession of pulses of up to 3 W average power, a 110 fs pulse width, and an 80 MHz repetition rate or up to 1 W average power, a 160 fs pulse width and an 80 MHz repetition rate at around 400 nm frequency-doubled wavelengths. Of course, other lasers can be used or optimized for use with writing refractive index changes into different optical materials in accordance with the marginal thresholds of the materials for undergoing localized refractive index changes without also undergoing optically induced damage such as significant light scattering or absorption that degrade their intended performance. The optical materials include ophthalmic hydrogel polymers (used in contact lenses and intraocular lenses) and cornea tissue (both excised and in vivo) as well as other ophthalmic materials that are naturally occurring or synthetically produced.

Scanners such as 140 and 150 can be arranged together with desired parameters for laser power, wavelength, and scan speed, to write millimeter-scale devices (preferably up to at least about 8 mm wide) in the optical material at speeds exceeding 100 mm/sec. Scanning operation may be under control of a controller 142, 174 based on inputs in accordance with desired refractive index structures to be written, based on calibration functions for a particular optical material for controlling laser exposures along a scan trace to obtain a desired refractive index profile in the optical material, by varying the laser power and/or relative scan speed along the scan region. Calibration functions for a specific type of optical material may be obtained by writing test patterns at known laser exposures and measuring resulting refractive index changes as described, e.g., in Gandara-Montano et al. "Femtosecond laser writing of freeform gradient index microlenses in hydrogel-based contact lenses," OPTICAL MATERIALS EXPRESS, Vol. 5, No. 10, pp. 2257-71, 1 Oct. 2015. A lateral gradient index microlens can be written in accordance with a calibration function by changing the scanning speed after each trace is written, and/or by changing the laser intensity before the next trace is written. In addition, the index of refraction is changed by varying beam intensity or the scan speed along the length of a trace or by some combination of the two. Both positive lenses and negative lenses (as opposed to cylindrical lenses) can be written using a combination of overlapping lenses and synchronous intensity control. The overall refractive power can be tailored to the desired shape using these parameters, as well as global positioning and the laser modulator.

In a particular embodiment useful for writing refractive corrections in ocular tissue in-vivo, a calibration function for laser writing such refractive corrections in live ocular tissue may be obtained by first writing test patterns in sections of test ocular tissue, such as enucleated ocular globes, and determining the induced refractive index in the written patterns relative to unmodified portions with an interferometer. More particularly, test patterns may be written in sections of one or more enucleated ocular globes with a femtosecond laser at different laser exposures for different sections of the test patterns, and the portions having test patterns written in them and surrounding areas may be dissected from the enucleated globes. The dissected portions may then be mounted into a wetcell with the portions placed in their natural curved orientation in the wetcell, and the induced refractive index change in the written patterns relative to unmodified tissue in the portions may be determined as a function of the laser exposure from interferograms taken of the mounted dissected portion with an interferometer.

In such calibration procedure, the test patterns may be written with a femtosecond laser at different laser exposures for different sections of the test patterns by varying the laser power and/or laser scan rate. The test patters may be written with a femtosecond laser, e.g., at different laser powers and constant scan rate for different sections of the test patterns, and/or at different laser scan rates and constant power for different sections of the test patterns.

The change in refractive index that can be effected by any one dose of actinic radiation in optical materials, such as corneal tissue or hydrogels, is limited by the damage thresholds of the materials. Generally, for the purpose of writing refractive index structures in such optical materials, with pulsed laser sources, the succession of pulses preferably have a pulse width between 8 fs and 500 fs, a pulse energy between 0.01 nJ and 10 nJ, a repetition rate between 10 MHz and 500 MHz, and a nominal wavelength between 400 nm and 1100 nm. These parameters are also tied to the focal spot size and the scanning rate at which the focal spot is moved relative to the optical material. For writing refractive index changes over larger volumes, both the focal spot size and the scanning rate are increased as much as practically possible in coordination with the other parameters that are set to operate in an energy regime just below the damage threshold of the material. Scanning speeds up to 10 m/s are contemplated.

Figure 3:
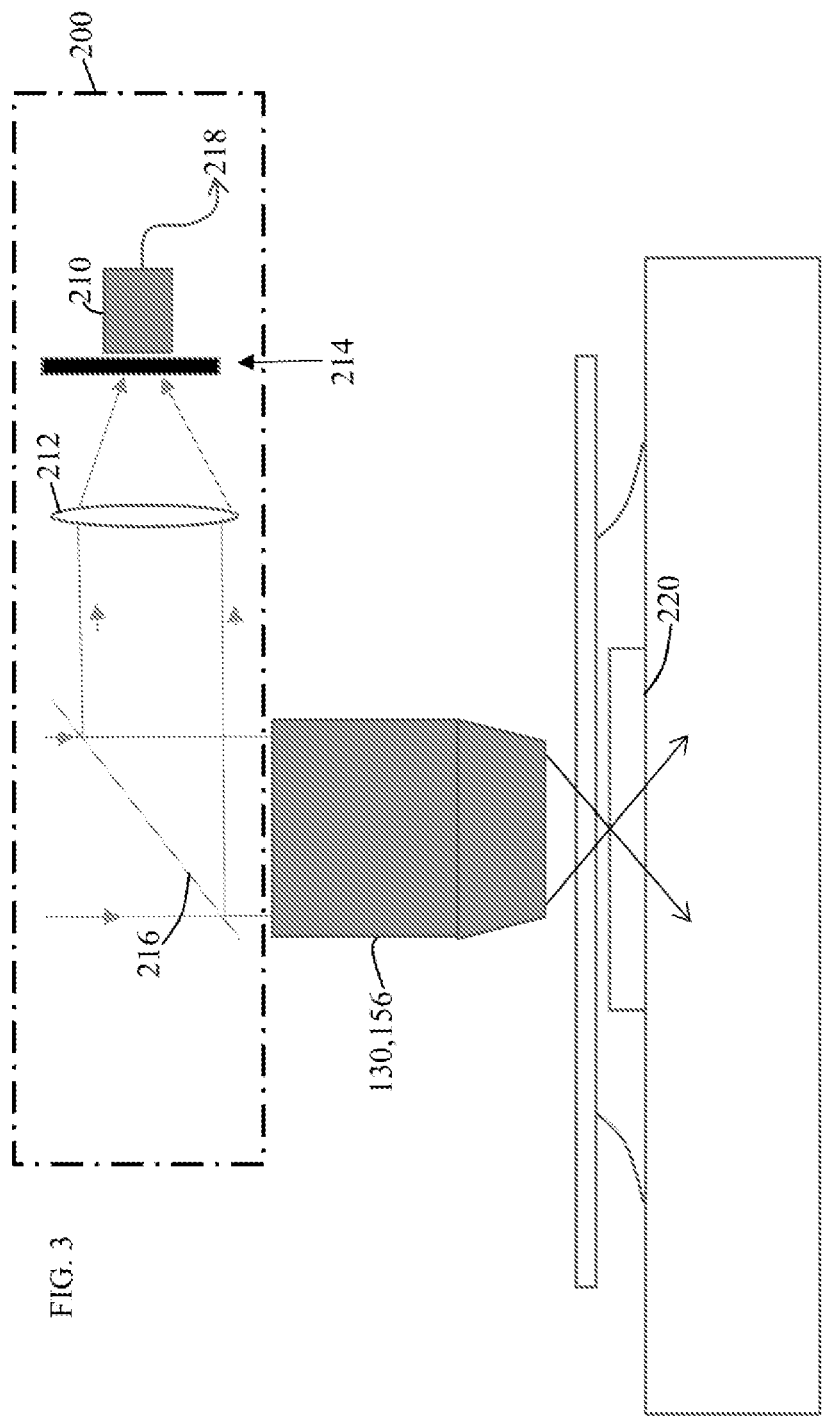
FIG. 3 is a diagram of part of a laser system including a real-time process control monitor that may be used in the present disclosure.

Further in accordance with embodiments of the present disclosure, as shown in FIG. 3 a real-time process control monitor 200 is employed for detecting emissions from the optical material 220 which are transmitted back through the objective lens 130, 156 at a second wavelength while writing the one or more traces with the pulsed laser output at the first wavelength. The real-time process control monitor 200 includes a photodetector 210, a lens 212 for focusing the emissions transmitted through the objective lens onto the photodetector, and a filter 214 for passing emissions at the second wavelength to the detector and blocking back-reflected pulse laser light of the first wavelength from the photodetector. Real-time process control monitor 200 may further include a reflector 216 such as a dichroic mirror or other beam splitter positioned in the path of the laser light and emissions from optical material to direct the emissions towards lens 212 and photodetector 210. The real-time process control monitor 200 may further be employed as a back-reflection monitor for detecting interfaces of the optical material for controlling depth of the laser focal spot by removing filter 214 or replacing such filter with a filter passing the back-reflected laser light of the first wavelength.

The output 218 of photodetector 210 may be sent to controller 142, 176 as shown in FIGS. 1 and 2, to provide further input for further controlling the laser exposure in response to an emission from the optical material at the second wavelength detected by the real-time process control monitor. Such further control enables an increased degree of safety in addition to control of the laser exposure in accordance with a pre-defined calibration function obtained for the specific type of optical material. In a particular embodiment, e.g., the controller may be configured to reduce or stop laser exposure along the one or more traces in response to a detected emission at the second wavelength outside a predetermined detected emission intensity range. Where such emissions are known to be associated with on-set of damage to the optical material, or known to occur just prior to damage to the optical material, monitoring the process to detect such emissions can be used to prevent subsequent damage to the optical material.

Figure 4:
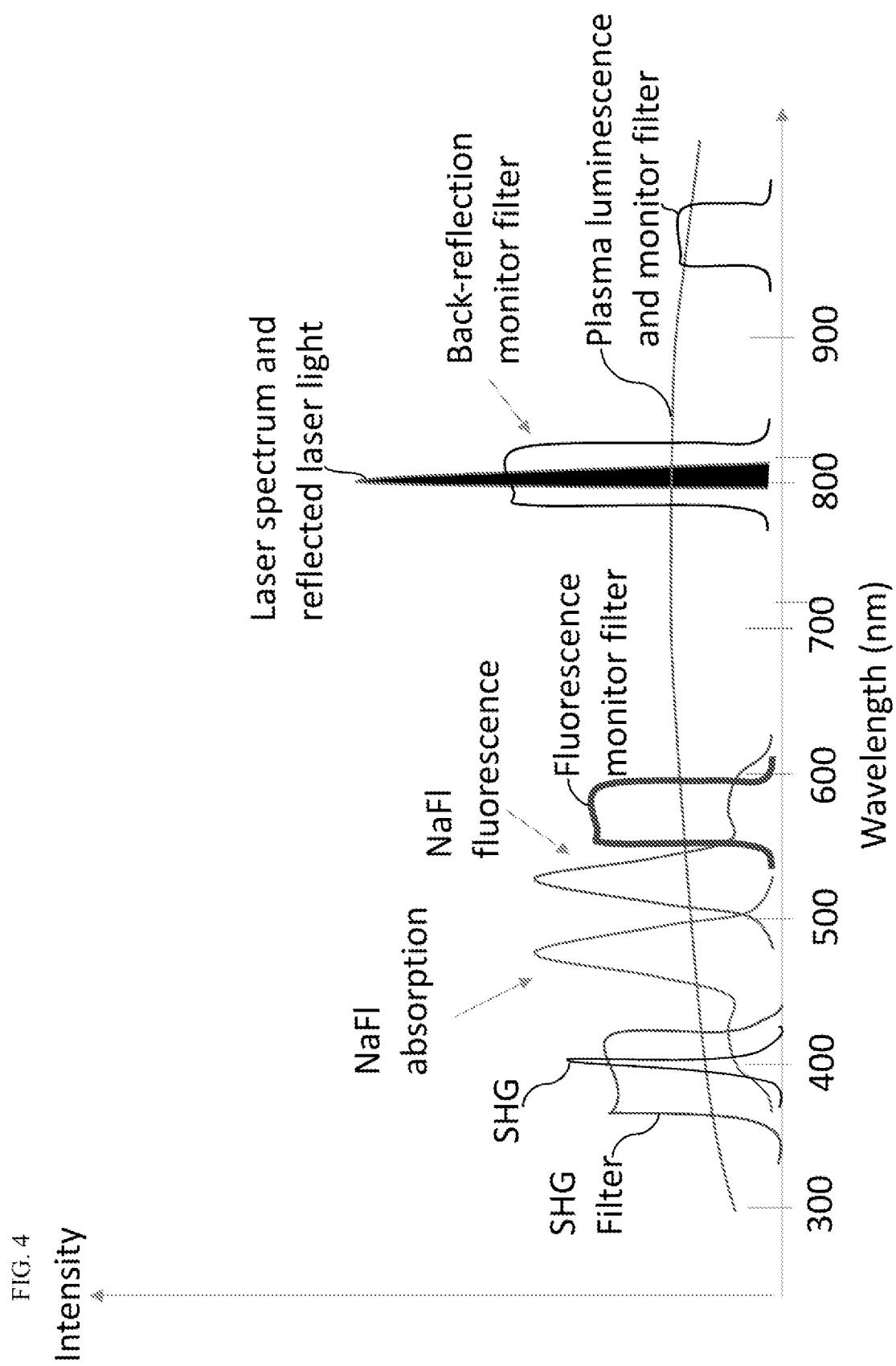
FIG. 4 is an illustration of back-reflected laser light and optical material emission wavelengths vs intensity, and filters for use in various embodiments of the present disclosure.

Plasma luminescence (e.g., broad wavelength band white sparks), e.g., has been observed to occur just before damage in some optical materials. In such case, filter 214 of real-time process control monitor 200 may be in the form of a filter which blocks laser light at a first wavelength (e.g., approximately 800 nm), while passing emission light at a second wavelength different than the first wavelength (e.g., approximately 950 nm), which is part of the plasma luminescence emission spectrum such as illustrated in FIG. 4. Real-time process control monitor 200 may be employed to monitor such plasma illuminescence during writing of refractive index structures in accordance with the present invention to provide a signal 218 prior to or at the onset of damage to the optical material, and further control such writing methods to prevent further damage (e.g., by immediately reducing laser intensity if plasma luminescence above a threshold level is detected). In a particular embodiment, e.g., a D/A output based on the photodetector signal and a pre-set output may be employed to reduce the laser power modulator (such as AOM) as soon as possible based on such detected signal.

Figure 5:
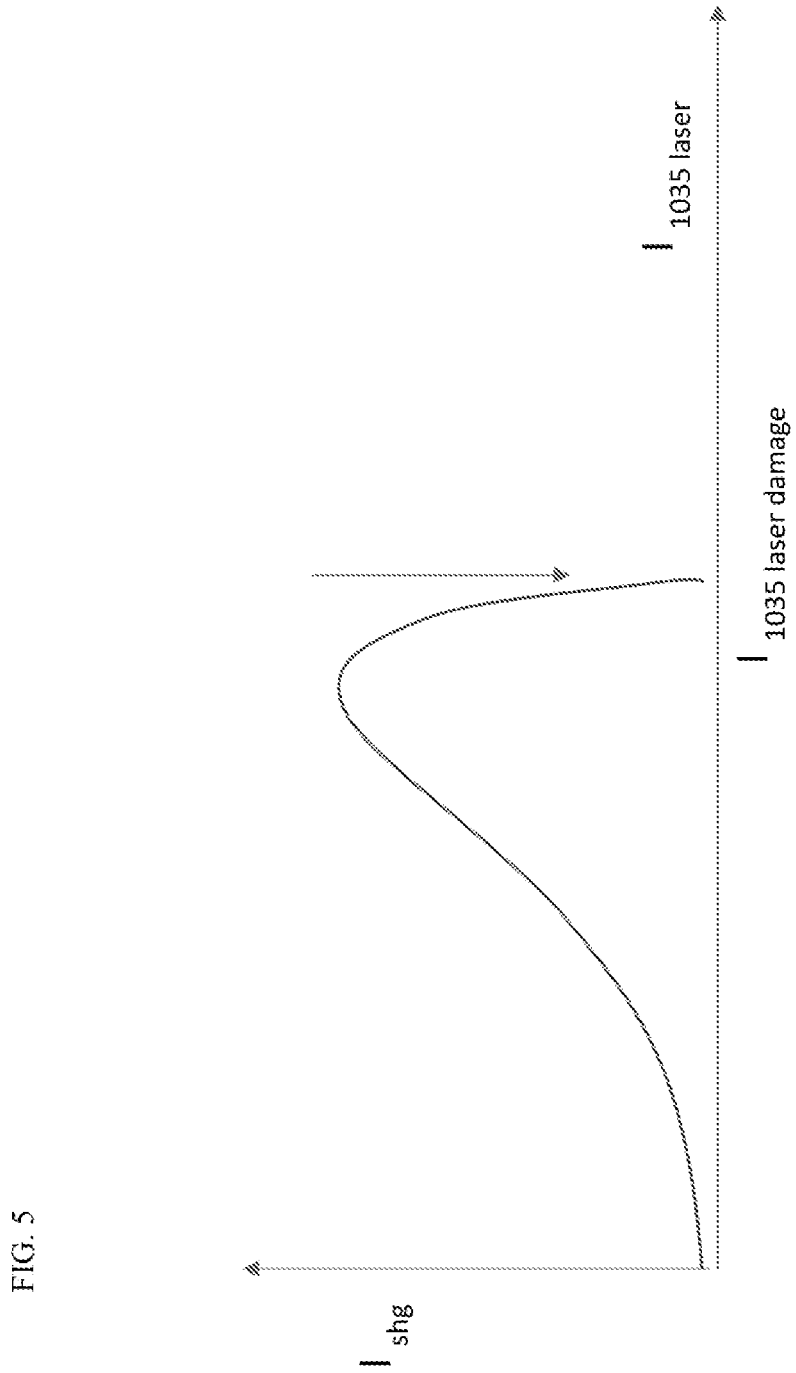
FIG. 5 is a graph of laser exposure intensity versus SHG intensity for cornea tissue in accordance with an embodiment of the present disclosure.

In a further embodiment, it has been observed that when the corneal stroma is exposed to laser light at a first wavelength, second harmonic generation (SHG) is generated at a second wavelength (i.e., at one-half the first wavelength) by the nearly hexagonal nanostructure of collagen fibrils of the corneal stroma. V. Nuzzo et al. ("In situ monitoring of second-harmonic generation in human corneas to compensate for femtosecond laser pulse attenuation in keratoplasty," Journal of Biomedical Optics, Vol. 12(6), 064032, November/December 2007), e.g., suggests determining penetration depth of a laser by evaluating back-scattered second-harmonic emission associated with the nonlinear optical properties of such tissue. It has now been further determined that IRIS femtosecond laser exposures results in highly localized loss of the typical corneal ultrastructure including disruption of the collagen fibrils. While SHG has been observed to initially increase with increasing laser exposure prior to such loss of typical corneal ultrastructure as diagramed in FIG. 5, SHG then decreases with higher laser exposure due to the loss of the corneal ultrastructure, and SHG ultimately goes to zero in damaged cornea regions. Real-time process control monitor 200 may be employed to monitor such SHG during writing of refractive index structures in accordance with the present invention to monitor such increase and decrease of SHG as tissue damage is approached, and further control such writing methods to prevent tissue damage (e.g., by immediately reducing laser intensity if a condition of anticipated tissue damage is approached based on such monitored SHG). As shown in FIG. 4, e.g., a filter passing SHG light at approximately 400 nm while blocking back-reflected laser light at approximately 800 nm may be employed in such embodiment.

In further embodiments, the real-time process control monitor 200 may further comprise one or more additional filter elements, such as an additional filter for selectively passing two-photon fluorescence emissions from the optical material transmitted through the objective lens to the detector, such as further illustrated in FIG. 4. In such embodiment, monitor 200 may further be used to monitor concentration of a fluorescing element prior to performance of the laser writing process, e.g., to monitor concentration of two-photon absorbing materials such as NaFl or riboflavin added to the optical material to increase the sensitivity of the material for laser energy absorption, similarly as described by L. Cui et al. in "High Resolution, Noninvasive, Two-Photon Fluorescence measurement of Molecular Concentrations in Corneal Tissue," IOVS, Vol. 52, No. 5, pp 2556-64, April 2011.

In embodiments wherein the real-time process control monitor 200 includes multiple filter elements for selectively passing different wavelengths of back reflected light or emissions to the photodetector, such filters may be positioned, e.g., on a motorized stage for selectively placing a desired filter in the path of back-reflected or emitted light from the optical material to the photodetector. Alternatively, or additionally, the path of light to the photodetector may be split spectrally to multiple photodetectors, or split spectrally to a single detector. Splitting the path of light to multiple photodetectors while employing multiple filter elements may be particularly useful for simultaneously monitoring several emission and/or back-reflected wavelengths of light. In each such embodiment, the photodetectors are each separate photodiodes.

Example 1. Phase Calibration IRIS Procedure for Writing in Ocular Tissue In Vivo The first step towards writing deterministic refractive structures in ocular tissue in vivo is metrology of the bulk optical phase change with respect to the delivered laser power for representative ocular tissue. This may be done in accordance with one embodiment by writing sets of phase bars, each at different laser powers with laser power constant across each individual bar, in whole, enucleated ocular globes. As an example, enucleate cat globes were obtained from Liberty Research, Inc. They were shipped overnight and the phase bars were written the next day. Between their removal from the animal and the writing of the phase bars, the eyes were stored in Optisol-GS (Bausch & Lomb, Inc.) and kept either refrigerated or on ice.

Figure 6:
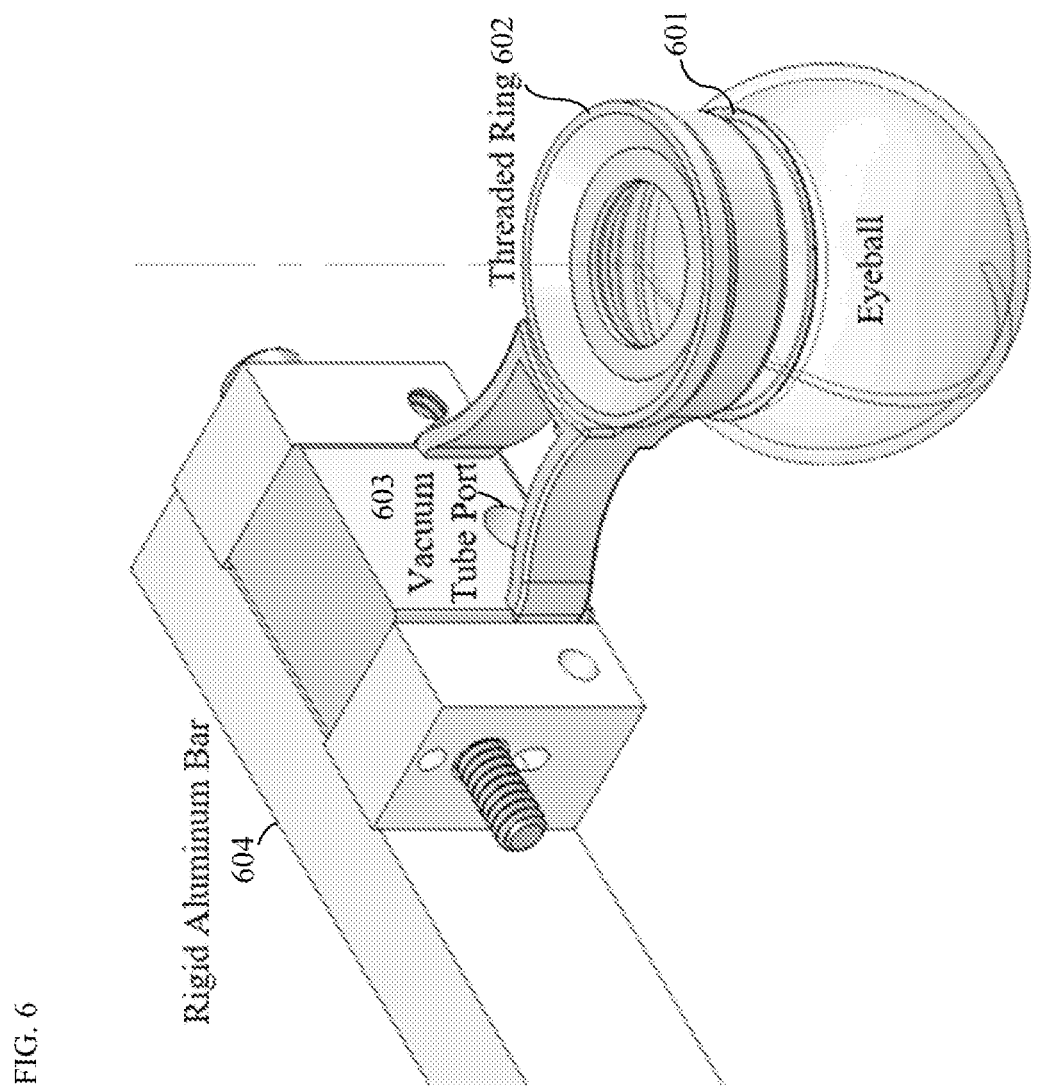
FIG. 6 is a CAD drawing of an applanator incorporating a curved eyeball interface, threaded ring clamp for a coverslip, and rigid aluminum bar for mounting to a table in accordance with an embodiment of the present disclosure.

In preparation for writing the phase bars with a writing system as shown in FIG. 1, the eyes were placed in conical depressions in a block of plastic, partially submerged in Optisol-GS, with the corneas oriented so that they were facing up. An applanator 601, shown in FIG. 6, was placed on the eye with a threaded ring 602 and vacuum was drawn through vacuum port 603 with a spring-loaded syringe (not shown). FIG. 6 is a CAD drawing of the applanator incorporating the curved eyeball interface, threaded ring clamp 602 for the applanator coverslip, and rigid aluminum bar 604 for mounting to a table. Once the cornea was suctioned to the applanator, the surface of the coverslip was found. This was done using a back-reflection monitor (BRM) composed of a singlet lens with a CCD camera located at the focal plane. The singlet lens collects the small amount of laser light that is reflected back through the objective and images it onto the CCD. When the focus of the objective is close to a surface, this image of the reflection approaches a small dot on the CCD. The surface is found by moving the objective vertically to adjust the distance between the objective and the applanator until the size of the image of the reflection from the coverslip-cornea interface is minimized. The surface was found at two points on either side of the applanated zone. As long as these points are within approximately 50 μm of each other, signifying that the objective plane of motion and the coverslip are tolerably parallel, then the locations are averaged and the average is used as the corneal surface location.

Figure 8:
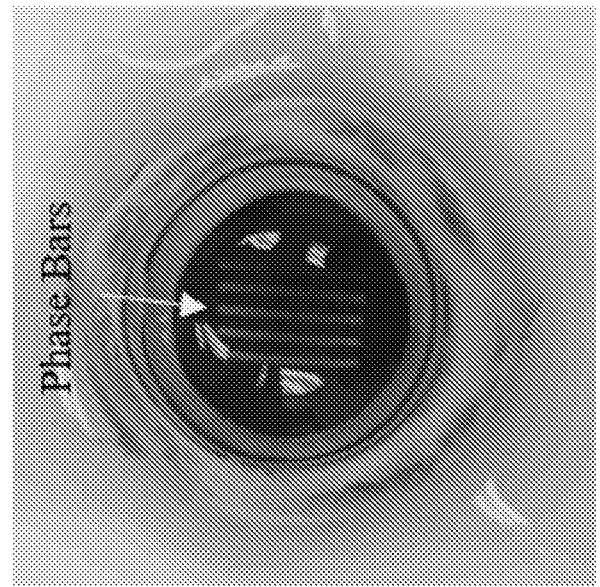
FIG. 8 shows a picture of an eyeball immediately after calibration bar writing in accordance with an embodiment of the present disclosure.
Figure 7:
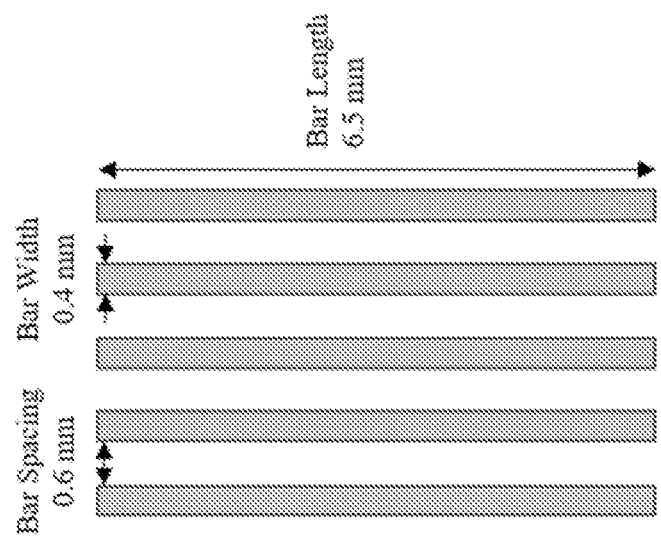
FIG. 7 shows a diagram of calibration bar geometry written in accordance with an embodiment of the present disclosure.

With the surface of the cornea found, the objective is moved to the starting location at one end of the set of phase bars and the bars are written. The parameters used for the calibration phase bars are given in Table 1. FIG. 7 shows a diagram of the calibration bar geometry, and FIG. 8 shows a picture of an eyeball immediately after writing. In addition to the parameters in Table 1, which were held constant, the laser power varied bar to bar to create a phase change calibration with respect to delivered laser power, which could then be converted to a calibration with respect to AOM voltage before writing the final, refractive structures.

TABLE 1

Writing Parameters for Phase Change Calibration Bars

| Parameter | Value |
| --- | --- |
| Bar width | 0.4 mm |
| Bar Spacing | 0.6 mm |
| Bar Length (measured) | 6.5 mm |
| Line Spacing | 0.5 μm |
| VC Drive Freqency | 10 Hz |
| VC Drive Voltage | 1.5 V |
| Beam Expansion Ratio | 1:4 |
| Pulse Width | 169 fs |
| # of Layers | 3 |
| Layer Spacing | 20 μm |

Figure 9:
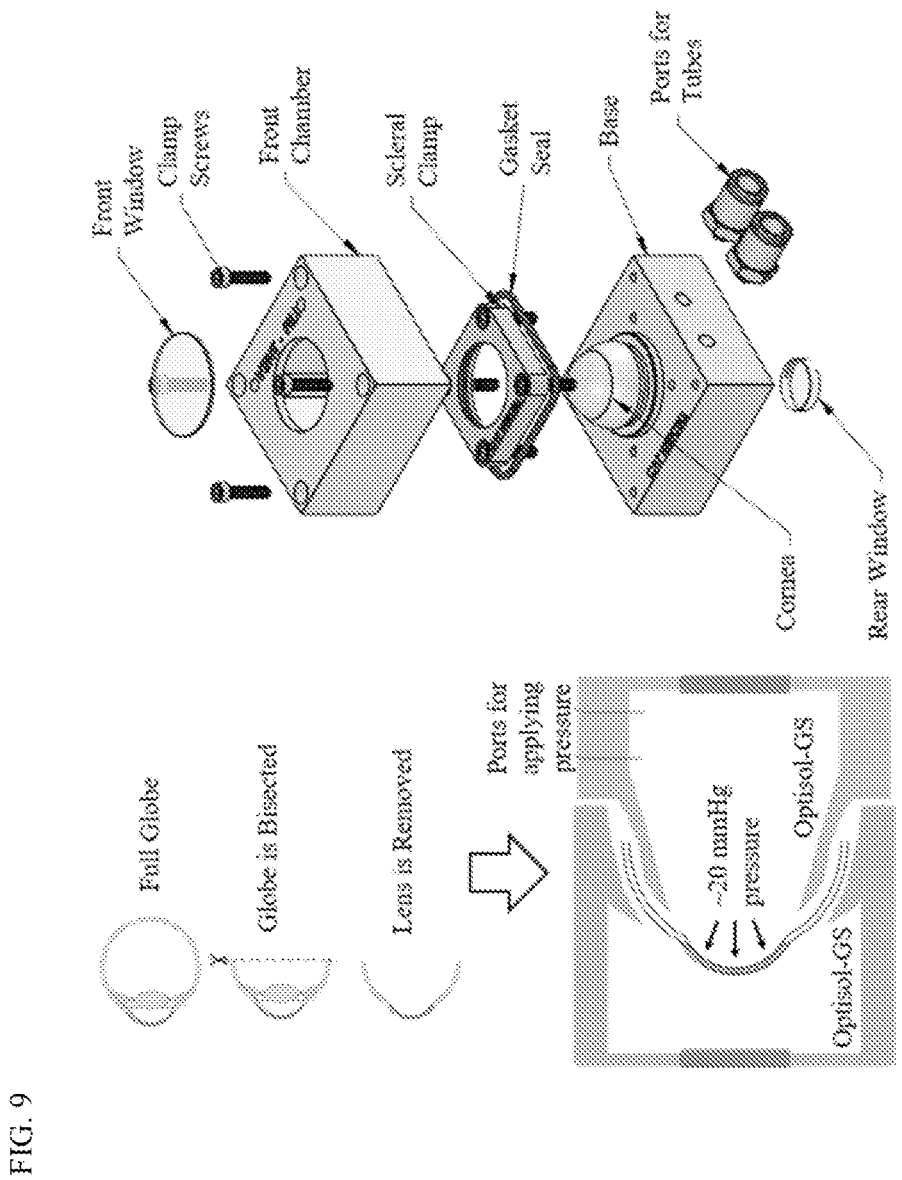
FIG. 9 shows a cartoon of the dissection and wetcell mounting of an enucleated eyeball as well as an exploded view of an actual wetcell design in accordance with an embodiment of the present disclosure.

Immediately after writing, many of the higher laser power calibration bars showed micro bubbles which could be seen both by eye and on an optical coherence tomography (OCT) imager. Once the calibration writing was finished, the eyeballs were wholly submersed in Optisol-GS and placed in the refrigerator for approximately an hour. This allowed the bubbles to dissipate, at which point the bars were completely transparent. After the bubbles dissipated, the eyeball was dissected. This was done by bisecting the eyeball approximately halfway between the cornea and the optic nerve. The retina, vitreous humor, aqueous humor, lens, and iris were removed, leaving only the cornea and approximately 4-8 mm of sclera surrounding the cornea. The cornea and surrounding sclera were then mounted into a custom wetcell. The wetcell was designed to fully submerse the cornea in fluid, either Optisol-GS or a saline solution, while the surrounding sclera was clamped to hold the cornea in place. Pressure could then be applied to the posterior surface of the cornea to mimic intraocular pressure (IOP), either through a tube hooked up to a syringe or simply by the hydrostatic pressure caused by elevating the tube to create a column of fluid. This put the cornea into its natural position, as in the eye, and smoothed out the wrinkles that result when there was not pressure applied. Windows were placed on the front and rear to allow for transmissive measurement with a Mach-Zehnder interferometer (MZI). A cartoon of the dissection and wetcell mounting as well as an exploded view of the actual wetcell design from SolidWorks are shown in FIG. 9. On left in FIG. 9 is a cartoon showing the dissection of the eye where the globe is bisected and the lens is removed. The remaining cornea and sclera is then mounted into a wetcell, with the cross-section of this shown in the bottom left. To the right in FIG. 9 is an exploded view taken from SolidWorks of the actual wetcell design showing how it was assembled.

Figures 10A, 10B:
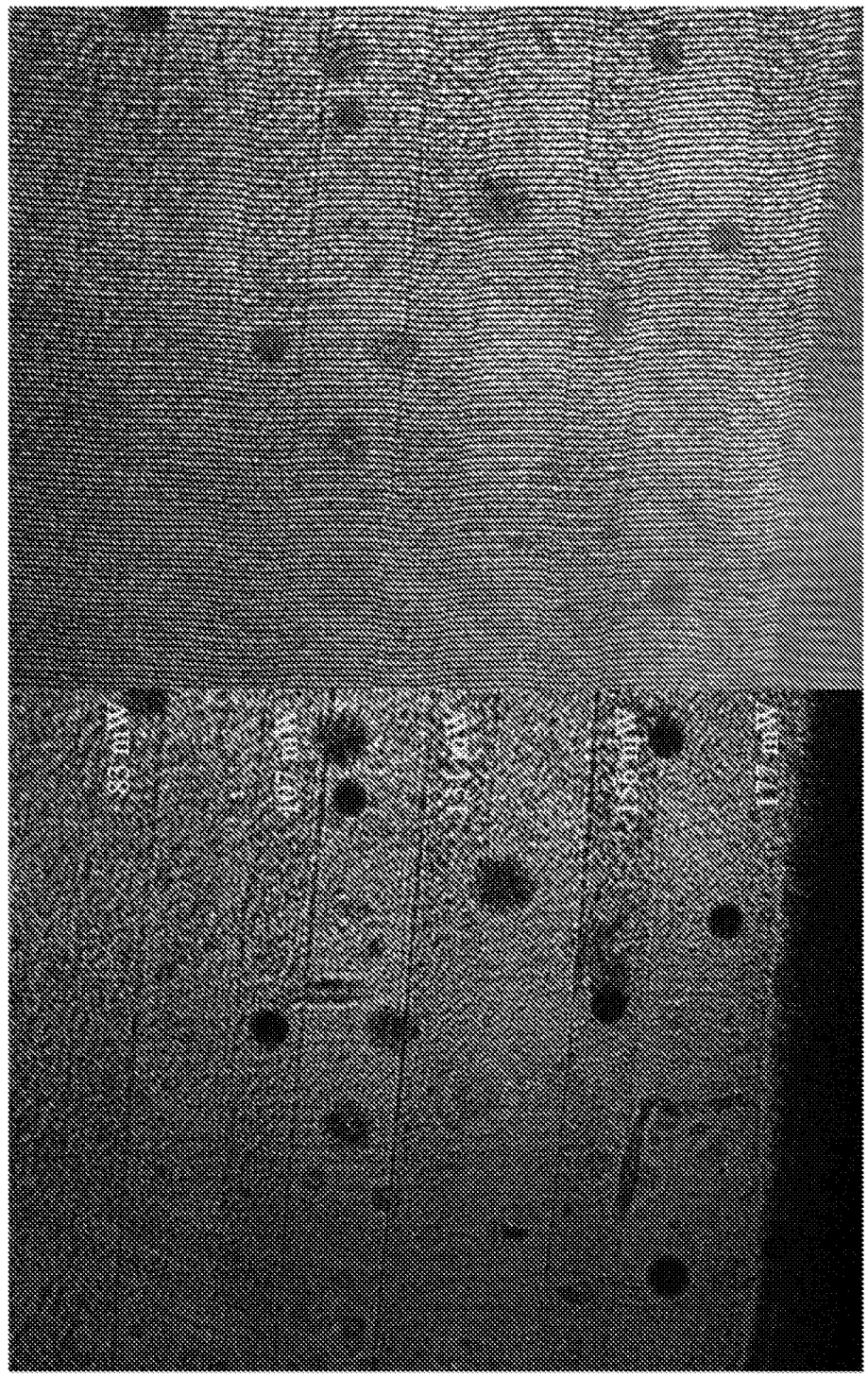
FIGS. 10a and 10b are Bright field (10a) and interferogram (10b) images of an example cornea mounted in a wetcell taken with a MZI in accordance with an embodiment of the present disclosure.

With the cornea mounted in a wetcell, transmissive measurement of the induced bulk optical phase change could be measured using a Mach-Zehnder Interferometer (MZI). The laser source used in the MZI measurements was a Helium-Neon (HeNe) laser operating at 632.8 nm. The wetcell-mounted cornea was placed on a platform attached to a manual XYZ translation stage in the measurement arm of the MZI. Multiple interferograms and collocated bright field images were taken of different set of bars. Example corresponding bright field (FIG. 10*a*) and interferogram (FIG. 10*b*) images of an example cornea mounted in the wetcell taken with the MZI can be seen in FIGS. 10*a* and 10*b*. The laser power delivered for each bar is given. The bright field images were taken simply by blocking the reference arm. The black spots are bubbles and residual debris from dissection floating the surrounding fluid.

Figure 11B:
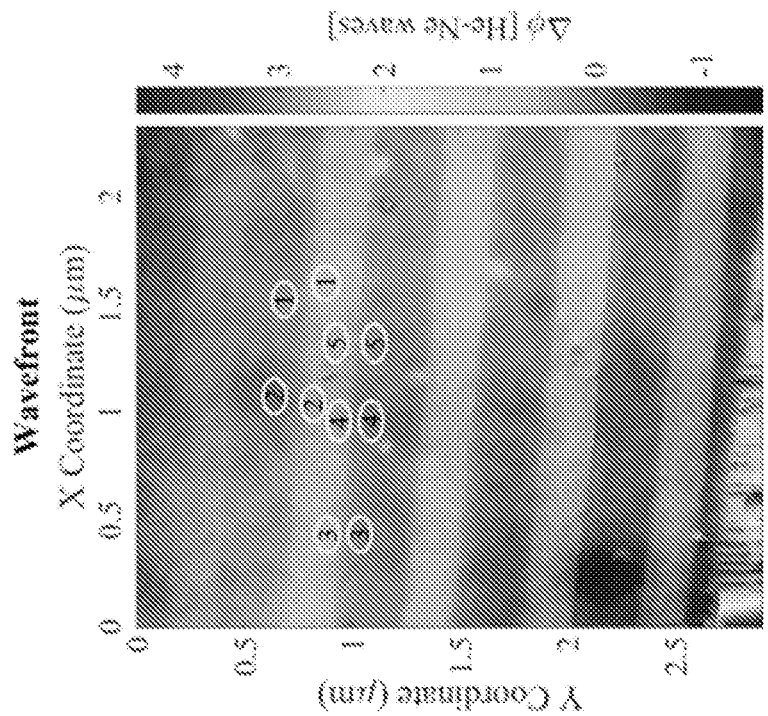
FIGS. 11a and 11b are images of an example phase map (FIG. 11b) processed from a corresponding interferogram (FIG. 11a) in accordance with an embodiment of the present disclosure.
Figure 11A:
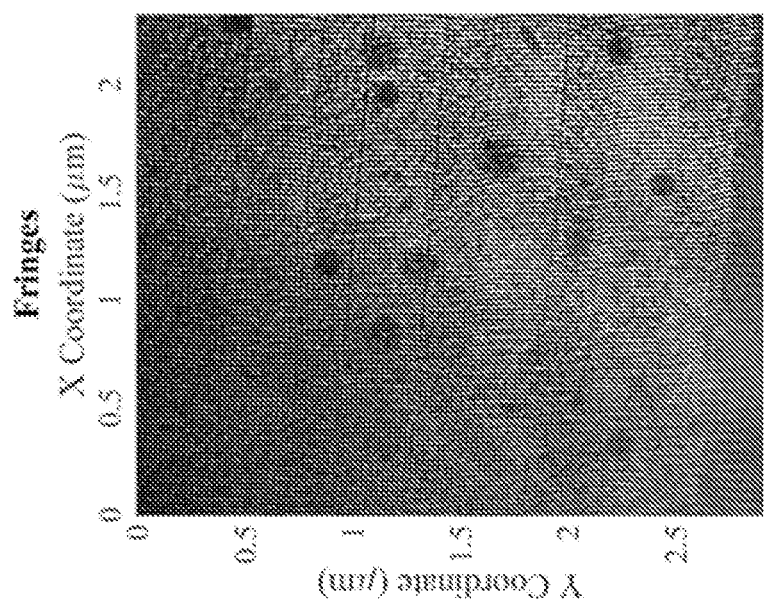

Once the interferograms were taken, they were processed into phase maps using a Fourier transform based algorithm described previously by Gandara-Montano, G. A., et al., *Femtosecond laser writing of freeform gradient index microlenses in hydrogel-based contact lenses*. Optical Materials Express, 2015. 5(10): p. 2257-2271, an example of which is shown in FIGS. 11*a* and 11*b*, where the example phase map (FIG. 11*b*) is processed from the corresponding interferogram (FIG. 11*a*). To calculate the phase change in each bar, small neighboring regions, one inside the bar and one outside the bar were averaged and the difference between the two was calculated. The regions taken had to be small and near each other due to low-frequency variation of the phase across the interferogram caused by residual aberrations and wrinkles in the cornea. To get an accurate assessment of the phase change induced at a given laser power, multiple pairs of small, neighboring regions were taken as shown in FIG. 11*b*. Examples of sets of neighboring pairs of regions that could be taken for calculating the resultant phase change is shown with the ellipses on the phase map. Each region has a number that denotes which pair it belongs to. Regions are taken along wrinkles or other low frequency variations to prevent those variations from entering into the calculated phase differences.

After finding the difference between multiple pairs of neighboring regions, the results from each individual bar were averaged to find the actual induced phase change at that power. This was done with two eyes from two different cats. The other eyes failed either in the IRIS writing process or in the wetcell mounting process. The final consolidated data from the successful eyes are show in FIG. 12. Each point in that plot corresponds to the average of approximately 10 different pairs of regions from a single bar and the standard deviations was found from the standard deviation of that average. The data was truncated at 160 mW delivered laser power. There seemed to be a saturation of the measured data above 160 mW. Each point corresponds to three layers of induced phase change. A linear fit was found for the truncated data and was used as the calibration curve for the design of the prescription for the in vivo creation of refractive structures in cats.

Example 2. Design of Refractive Corrections

After the calibration curve was found, the next step toward writing a full structure in vivo in a cat was to design the lens that would be written. The most fundamental way to describe a lens is through the accumulated optical phase of a wavefront. The nonlinear nature of the IRIS process would suggest that the region of RI change thickness was <10 μm. This is thin enough that the IRIS structure could be reasonable treated as a thin lens, which can be treated as a phase transformation represented by $$t_l(r) = e^{-i\frac{kr^2}{2f}} \quad (1)$$

where k is the wavenumber in freespace, r is the radial position in the lens, and f is the focal length of the lens. The phase change profile to create a lens using the calibration from the previous section is therefore $$\Delta\phi(r) = \frac{kr^2}{2f}. \quad (2)$$

This phase is in units of radians. By converting to variables that are more widely recognizable in the ophthalmological field and converting the units to waves at a design wavelength, we find $$\Delta\phi(r) = \frac{Dr^2}{2\lambda}, \quad (3)$$

where D is the optical power of the lens in Diopters and λ is the design wavelength. For clinical relevance, the power of the lens must have a magnitude of at least 1.5 D (f=666.7 mm). Using equation (3) with a design wavelength of 633 nm, a 1.5 D lens over the clinically relevant optical zone of 6.0 mm yields a maximum phase change of 10.66 waves at 633 nm. This is significantly higher than the IRIS process could achieve in cornea.

While the total magnitude of the phase difference over the full structure is much too great for IRIS, it is possible to wrap the phase at 1 wave intervals. This would create a structure with a 1 wave maximum phase difference across the structure while maintaining the same optical power. This type of structure is called a Fresnel Lens, also known as a kinoform lens. By collapsing the phase in this way, the result is a structure with a series of zones with phase wrapping between 0 and 1 wave. A comparison of cross-sections of the required accumulated phase for a −1.5 D lens across a 6 mm diameter region with a standard phase profile (S) and a Fresnel lens type phase profile (F) can be seen in FIG. 13.

The phase Fresnel lens works as a diffractive optical element (DOE). With DOEs, the focus is dependent on the number of zones, with more tightly spaced zones resulting in a more powerful lens. This is beneficial for writing a lens using IRIS because, while the optical phase change induced was characterized, the uncertainty in the calibration was relatively large. However, if the peak phase change is not equal to an integer number of waves, the diffraction is not perfectly matched and the light will be directed into different diffractive orders, corresponding to different foci along the optical axis. These foci are located at integer multiples of the first order focus location. This creates what is called a multi-focal optic, which has been leveraged for design of IOLs for people with presbyopia. The amount of light sent into the different orders, or diffraction efficiency, can be calculated using $$\eta(m,\mu) = \text{Sinc}^2[\pi(m-m_0\mu)] \quad (4)$$

where m is the diffracted order of interest, $m_0$ is the design order, and μ is a parameter determined by the departure from the design zone height. In the case of the structures used in this design, μ can be calculated with $$\mu = \frac{h}{h_0} \times \frac{\lambda_0}{\lambda} \quad (5)$$

where h is the peak-to-valley phase height of the structure, $h_0$ is the design phase height to send everything to the design order, $\lambda_0$ is the design wavelength, and λ is the measurement or observation wavelength. With μ=1, η is 1 for the design order and 0 for all other orders.

Figure 12:
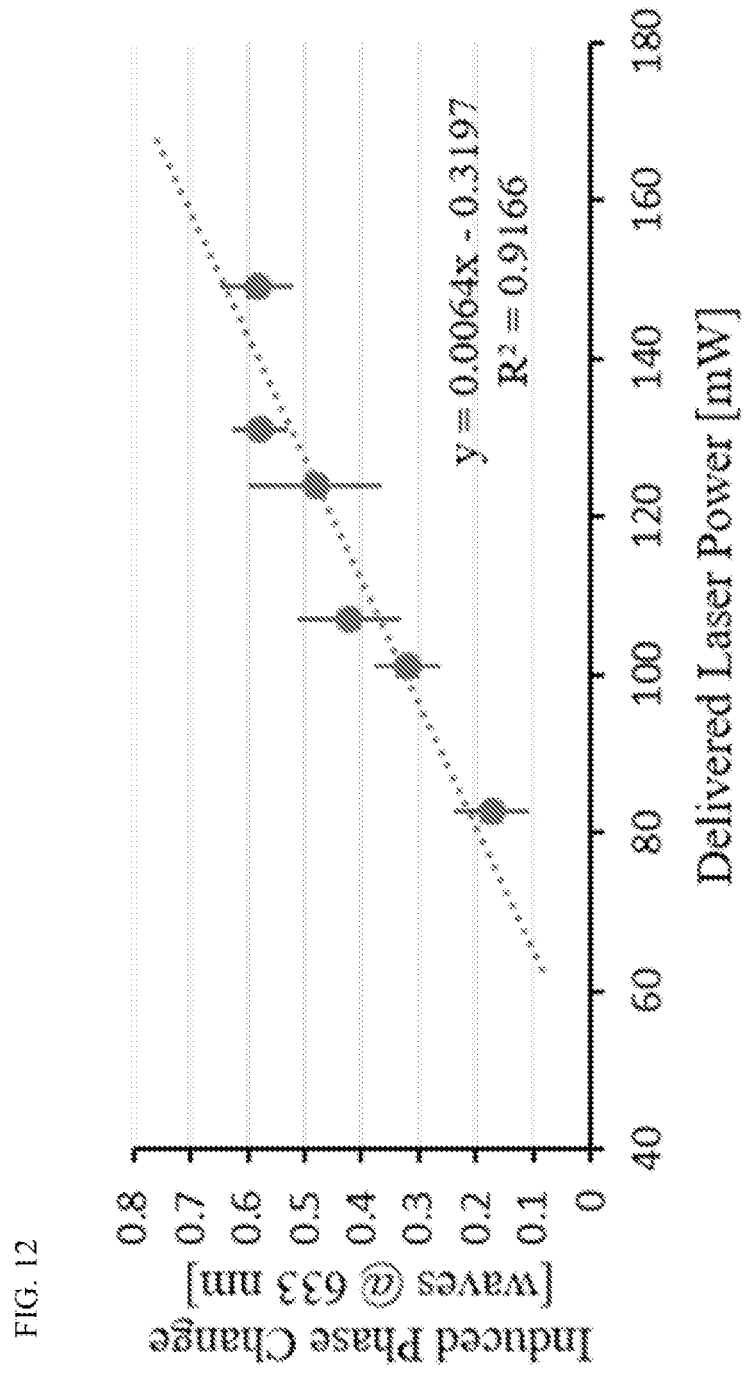
FIG. 12 is a plot of the induced bulk phase change in enucleated cat eyes as a function of delivered laser power in accordance with an embodiment of the present disclosure.
Figure 13:
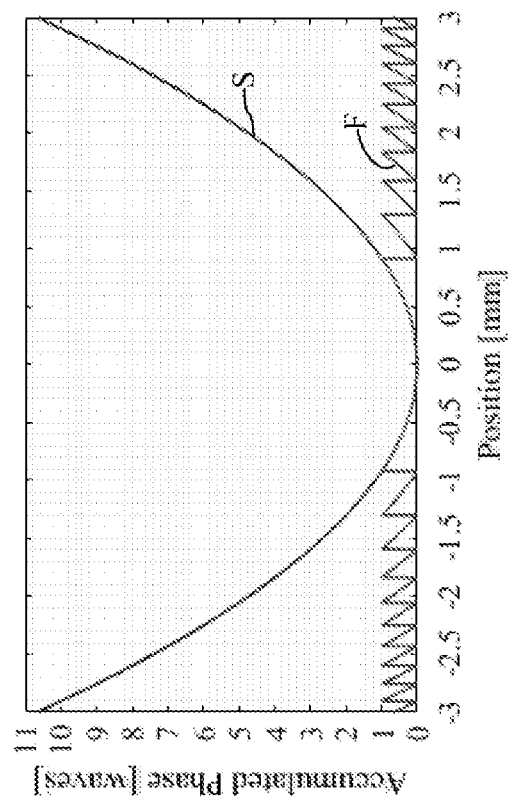
FIG. 13 illustrates a comparison of cross-sections of the required accumulated phase for a −1.5 D lens across a 6 mm diameter region with a standard phase profile (S) and a Fresnel lens type phase profile (F).

The Fresnel phase profile shown in FIG. 13 was converted to an incident laser power using the fit equation from FIG. 12. This was used as the laser power prescription in one dimension for the design of the IRIS structure. The structure was designed as a cylindrical Fresnel lens, with the prescription governing the laser power delivered along the x- (linear stage-) axis, and the laser power remaining constant along the y- (flexure stage-) axis. The software was developed such that an AOM voltage to laser power calibration could be loaded onto the computer on the day of writing and the software would convert the laser power at a position into an AOM voltage in real time.

Example 3. In Vivo IRIS Procedure

One eye each from two different young adult domestic short hair cats were used for in vivo IRIS experiments. The cats were behaviorally trained in the months leading up to the IRIS procedure to fixate in a custom Shack-Hartmann wavefront sensor (SHWS) that has previously been described (Huxlin, K. R., et al., *Monochromatic ocular wavefront aberrations in the awake-behaving cat*. Vision Research, 2004. 44(18): p. 2159-2169, and Nagy, L. J., et al., *Photorefractive keratectomy in the cat eye: Biological and*

*optical outcomes.* Journal of Cataract & Refractive Surgery, 2007. 33(6): p. 1051-1064). Prior to the IRIS procedure several different wavefronts were collected using the SHWS to construct a baseline wavefront for the cat to which the wavefronts post-IRIS could be compared. At least one week pre-IRIS, OCT images were obtained of each eye.

For the IRIS procedure, the cats were put under surgical (ketamine, 5 mg/kg, dexmedetomidine hydrochloride 0.04 mg/kg) and topical anesthesia (proparacaine 0.5%; Falcon). The cat was then fixed under the objective using a titanium headpost attached to the cat's skull. The headpost was attached with a dowel pin to a 3-axis manual stage with the attach point itself designed to provide rotation about the axis of the headpost. The cornea was applanated using the applanator shown in FIG. 6. The parameters for writing the IRIS Fresnel structure were the same as those listed in Table 1 except for bar size parameters which were not applicable. The Fresnel lens was designed to be 5.9 mm in diameter. The flexure based scanning system operated over a 6.5 mm by 6.0 mm region with all points outside the 5.9 mm circular Fresnel lens set to zero laser power through the AOM. Before mounting the cat, an AOM voltage to delivered laser power calibration curve was measured. This curve was used to create the AOM voltage prescription corresponding to the Fresnel structure shown in FIG. 13. With the cat mounted and the prescription calculated, the IRIS procedure was performed with a total runtime for all three layers of 30 minutes.

Once the IRIS procedure was complete, the applanator was removed from the eye and the cat was unmounted from the system. The eyes were then immediately imaged with the OCT imager. Once the cats recuperated enough from anesthesia to cooperate with wavefront measurements, each eye was measured using the SHWS. This recuperation usually took 1-2 days. Wavefronts were then measured periodically over the following 6 months.

Zernike Polynomials were used to describe the reconstructed wavefront, in accordance with standards for reporting ophthalmological aberrations. The Zernike coefficients will be referred to as $C_j$ where j is the represents the index of a specific Zernike coefficient. The most important Zernike terms for Ophthalmological aberrations are $C_4$, representing defocus, and $C_3$ and $C_5$, representing the two astigmatism terms. The relations governing the conversion from these Zernike coefficients to the corresponding optical powers are $$DEF = \frac{4\sqrt{3}\,C_4}{r^2}, \tag{6}$$

$$CYL = -\frac{4\sqrt{6}\,\sqrt{(C_3)^2 + (C_5)^2}}{r^2}, \tag{7}$$

and $$\phi = \frac{1}{2}\tan^{-1}\left(\frac{C_3}{C_4}\right) \tag{8}$$

where DEF is the paraxial wavefront defocus, CYL is the paraxial wavefront cylinder, $\phi$ is the angle of the cylinder axis, and r is the radius of the measurement zone. These equations are of opposite power from the traditional ophthalmological representation because it is the second-order optical power, not the spectacle correction, that is of interest. In addition to the optical powers, it is often of interest to quantify the overall higher-order aberrations. This is often represented with the root mean square (RMS) which is given by $$RMS = \sqrt{\sum_j (C_j)^2}. \tag{9}$$

To quantify the higher-order aberrations, the sum in Eq. 9 is taken from j=6 to 65 and is call the higher-order root mean square (NORMS).

Figure 14:
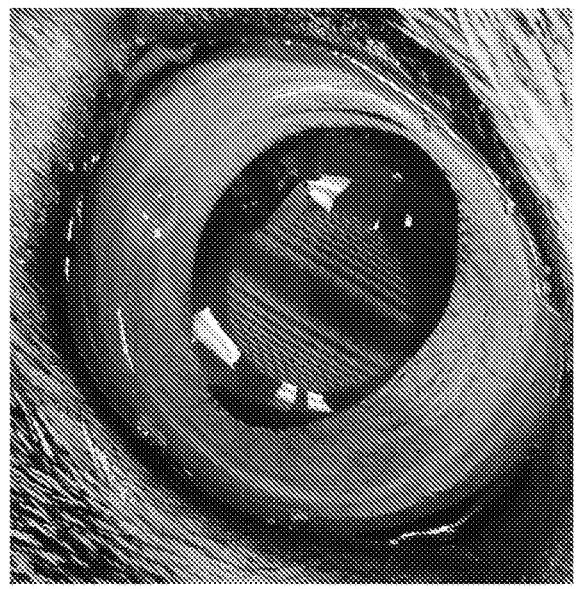
FIG. 14 is a picture of a cylindrical Fresnel lens written by IRIS in a living cat in accordance with an embodiment of the present disclosure.

Immediately after the IRIS procedure was performed, a picture was taken of the eye, one of which can be seen in FIG. 14. Microbubbles were visible in the cornea immediately after the procedure was performed. However, these bubbles dissipated over the following 30-60 minutes, leaving the cornea completely transparent. In the case of the Fresnel lens, these bubbles made the phase-wrapped structure immediately apparent as the bubbles only formed in the higher phase change regions (where the most laser power was delivered.)

Figure 15:
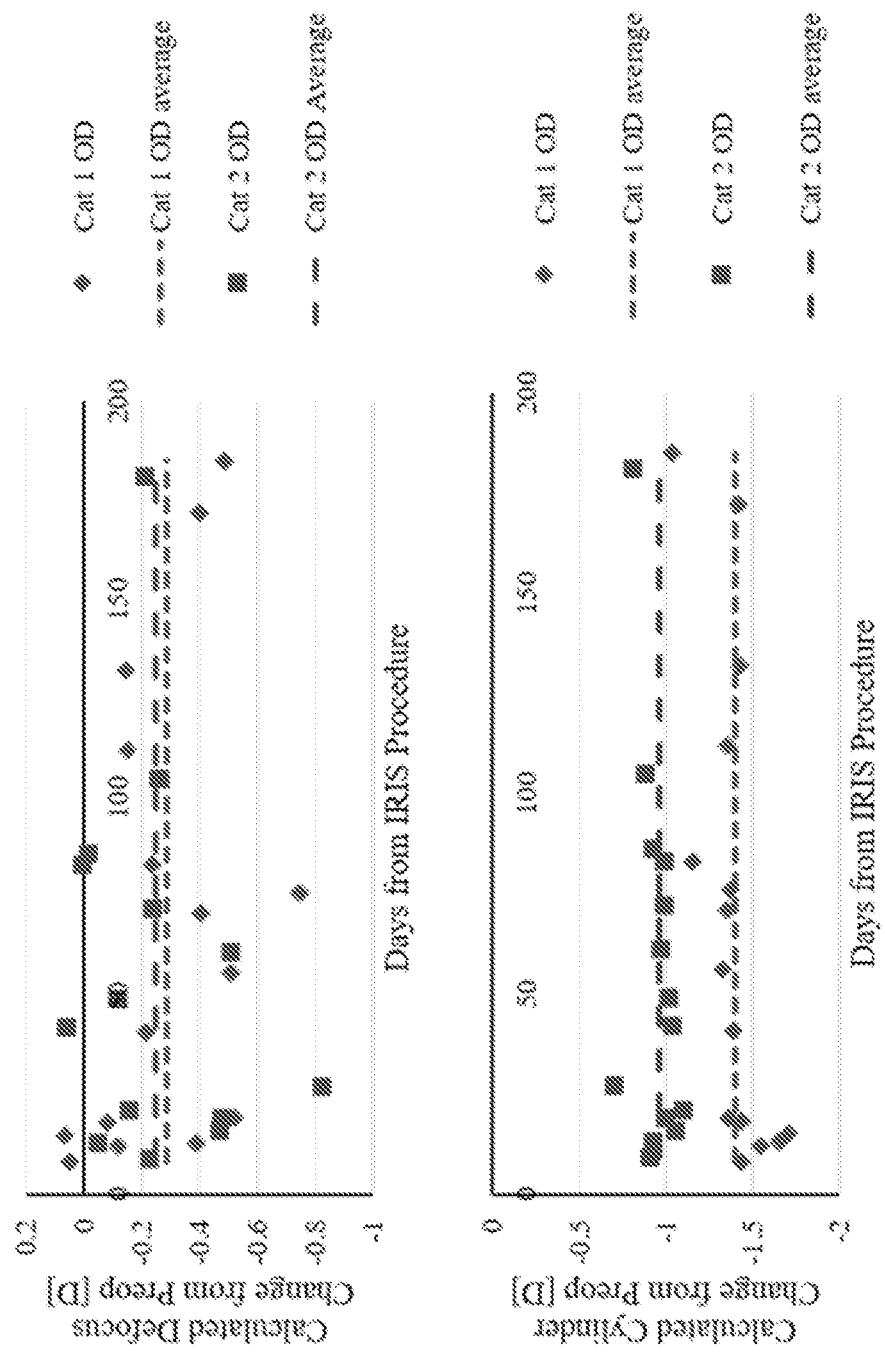
FIG. 15 shows plots of the change from preoperative wavefronts for defocus (top) and cylinder (bottom) power of a cylindrical Fresnel lens written by IRIS in a living cat in accordance with an embodiment of the present disclosure.

Over the following six months the cylindrical power calculated from the SHWS wavefront data remained stable for both eyes; however, a small difference in the magnitude of induced cylinder was measured between the two eyes The average cylindrical power difference from the baseline wavefront was −1.40±0.17 D for one cat and −0.96±0.10 D for the second cat. These values were stable over the six month measurement timeframe. The defocus was variable but centered around approximately −0.25 D for both eyes. The data are summarized in Table 2 and a plot of both data sets of both defocus and cylinder are shown in FIG. 15.

TABLE 2

Summary of measured Zernike coefficients and calculated refractive powers

| Parameter | Cat 1 OD | Cat 2 OD |
|---|---|---|
| Δ Zernike Coefficients [μm] | | |
| ΔC3, astigmatism at 45° | −0.41 ± 0.07 | −0.15 ± 0.10 |
| ΔC4, defocus | −0.26 ± 0.21 | −0.22 ± 0.22 |
| ΔC5, astigmatism at 0° | −0.79 ± 0.11 | −0.76 ± 0.27 |
| ΔHORMS [μ] | 0.50 ± 0.10 | 0.37 ± 0.04 |
| ΔRefractive Power [D] | | |
| ΔDefocus | −0.29 ± 0.23 | −0.24 ± 0.24 |
| ΔCylinder | −1.40 ± 0.17 | −0.96 ± 0.10 |

An entire process for creating in vivo refractive corrections has been presented, from system calibration to structure design to the final in vivo procedure and metrology. A calibration between phase change and delivered laser power was found using enucleated eyes measured in a wet cell with an MZI. This calibration showed a mostly linear trend up to a saturation point between 0.6 and 0.8 waves of induced phase change. This calibration was used to design a −1.5 D refractive corrector in the form of a Fresnel Lens type structure. Finally, using the IRIS process, the designed Fresnel lens was made in the eyes of two living cats, producing final refractive corrections of −1.40±0.17 D and −0.96±0.10 D with very little induced defocus. These corrections were measured over the course of six months with a SHWS and were stable over that time. While the described experiments have been performed with cats, similar refractive index change is possible in humans.

The described enucleated globe calibration method for formulating a calibration function for in vivo laser writing systems may be used with or without further real time process control embodiments also described herein.

Further details of scanning systems useful in the present disclosure are described in US Patent Application Publication No. 20160144580 A1 entitled HIGH NUMERICAL APERTURE OPTOMECHANICAL SCANNER FOR LAYERED GRADIENT INDEX MICROLENSES, METHODS, AND APPLICATIONS, which is hereby incorporated by reference. Further exemplary suitable methods and techniques for refractive index writing in optical materials have been described, for example, in U.S. Pat. No. 7,789,910 B2, OPTICAL MATERIAL AND METHOD FOR MODIFYING THE REFRACTIVE INDEX, to Knox, et. al.; U.S. Pat. No. 8,337,553 B2, OPTICAL MATERIAL AND METHOD FOR MODIFYING THE REFRACTIVE INDEX, to Knox, et. al.; U.S. Pat. No. 8,486,055 B2, METHOD FOR MODIFYING THE REFRACTIVE INDEX OF OCULAR TISSUES, to Knox, et. al.; U.S. Pat. No. 8,512,320 B1, METHOD FOR MODIFYING THE REFRACTIVE INDEX OF OCULAR TISSUES, to Knox, et. al.; and U.S. Pat. No. 8,617,147 B2, METHOD FOR MODIFYING THE REFRACTIVE INDEX OF OCULAR TISSUES. All of the above named patents, including the '910, '553, '055, '320, and '147 patents are incorporated herein by reference in their entirety for all purposes.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A refractive index writing system comprising:
a pulsed laser source for providing a pulsed laser output at a first wavelength;
an objective lens for focusing the pulsed laser output to a focal spot in an optical material;
a scanner for relatively moving the focal spot with respect to the optical material at a relative speed and direction along a scan region for writing one or more traces in the optical material defined by a change in refractive index; and
a controller for controlling laser exposures along the one or more traces in accordance with a calibration function for the optical material to achieve a desired refractive index profile in the optical material by varying a laser power and/or relative scan speed for maintaining an energy profile within the optical material along the scan region above a nonlinear absorption threshold of the optical material and below a breakdown threshold of the optical material at which significant light scattering or absorption degrades an intended performance of the optical material;
wherein the refractive index writing system is for writing traces in in vivo optical tissue, and the controller is configured with a calibration function obtained by calibrating refractive index change induced in test ocular tissue by femtosecond laser writing as a function of laser exposure by: writing test patterns in sections of one or more enucleated ocular globes with a femtosecond laser at different laser exposures for different sections of the test patterns; and determining the induced refractive index change in the written patterns relative to unmodified tissue in areas surrounding the written patterns as a function of the laser exposure from interferograms taken of the written patterns and surrounding areas in their natural curved orientation.

2. The writing system of claim 1, wherein the calibration function is obtained by calibrating refractive index change induced in test ocular tissue by femtosecond laser writing as a function of laser exposure by:
writing test patterns in sections of one or more enucleated ocular globes with a femtosecond laser at different laser exposures for different sections of the test patterns;
dissecting portions of the one or more enucleated ocular globes including the sections having test patterns written in them and surrounding areas from the enucleated globes;
mounting the dissected portions into a wetcell with the portions placed in their natural curved orientation in the wetcell; and
determining the induced refractive index change in the written patterns relative to unmodified tissue in the portions as a function of the laser exposure from interferograms taken of the mounted dissected portion with an interferometer.

3. The writing system of claim 1 in which the pulsed laser source is arranged for producing a collimated output beam composed of a succession of pulses having a pulse energy between 0.01 nJ and 10 nJ, a pulse duration between 8 fs and 500 fs, and a repetition rate between 10 MHz and 500 MHz.

4. The writing system of claim 1, further comprising a real-time process control monitor for detecting emissions from the optical material transmitted through the objective lens at a second wavelength while writing the one or more traces, comprising a photodetector, a lens for focusing the emissions transmitted through the objective lens onto the photodetector, and a filter for passing emissions at the second wavelength to the detector and blocking back-reflected pulse laser light of the first wavelength from the photodetector; and wherein the controller is further configured for further controlling the laser exposure in response to an emission from the optical material at the second wavelength detected by the real-time process control monitor.

5. The writing system of claim 4, wherein the controller is configured to reduce or stop laser exposure along the one or more traces in response to a detected emission at the second wavelength outside a predetermined detected emission intensity range.

6. The writing system of claim 5, wherein the process control monitor is configured to detect plasma luminescence emissions at the second wavelength.

7. The writing system of claim 5, wherein the process control monitor is configured to detect backscattered second harmonic generation at the second wavelength.

8. The writing system of claim 4, wherein the real-time process control monitor comprises multiple filter elements for selectively passing different wavelengths of back reflected light or emissions to the photodetector.

9. The writing system of claim 4, wherein the real-time process control monitor comprises multiple filter elements and multiple photodetectors for simultaneously detecting back reflected light or emissions at different wavelengths.

10. The writing system of claim 9 in which the photodetectors are each photodiodes.

11. The writing system of claim 4 in which the photodetector is a photodiode.

12. The writing system of claim 4, wherein the real-time process control monitor further comprises an additional filter for selectively passing two-photon fluorescence emissions from the optical material transmitted through the objective lens to the detector.

13. The writing system of claim 1, further comprising an ocular patient interface comprising a vacuum suction ring for coupling the writing system to a cornea of a patient.

14. A method of writing localized refractive index changes in optical materials with a pulsed laser source providing a pulsed laser output at a first wavelength within energy regimes above a nonlinear absorption threshold of the optical materials and below a breakdown threshold of the optical materials at which significant light scattering or absorption degrades their intended performance, wherein the method employs a refractive index writing system in accordance with claim 1 and comprising steps of:
    producing a collimated output beam composed of a succession of pulses having a pulse energy between 0.01 nJ and 10 nJ, a pulse duration between 8 fs and 500 fs, and a repetition rate between 10 MHz and 500 MHz;
    focusing the beam with an objective lens to a focal spot within the optical material;
    relatively moving the objective lens with respect to the optical material at a relative speed and relative direction to write one or more traces defined by a change in refractive index of the optical material; and
    controlling laser exposures along the one or more traces in accordance with a calibration function for the optical material to achieve a desired refractive index profile in the optical material by varying a laser power and/or relative scan speed to maintain an energy profile within the optical material along a scan region above a nonlinear absorption threshold of the optical material and below a breakdown threshold of the optical material at which significant light scattering or absorption degrades an intended performance of the optical material;
    wherein the optical material is in vivo optical tissue, and further comprising wherein the calibration function for the optical material is obtained by calibrating refractive index change induced in test ocular tissue by femtosecond laser writing as a function of laser exposure by: writing test patterns in sections of one or more enucleated ocular globes with a femtosecond laser at different laser exposures for different sections of the test patterns; and determining the induced refractive index change in the written patterns relative to unmodified tissue in areas surrounding the written patterns as a function of the laser exposure from interferograms taken of the written patterns and surrounding areas in their natural curved orientation.

15. The method of claim 14, further comprising detecting emissions from the optical material transmitted through the objective lens at a second wavelength while writing the one or more traces by focusing the emissions transmitted through the objective lens onto a photodetector and blocking back-reflected pulse laser light of the first wavelength from the photodetector; and further controlling the laser exposure in response to a detected emission from the optical material at the second wavelength.

16. The method of claim 15, wherein the laser exposure is reduced or stopped along the one or more traces in response to a detected emission at the second wavelength outside a predetermined detected emission intensity range.

17. The method of claim 16, wherein the detected emission at the second wavelength is plasma luminescence.

18. The method of claim 16, wherein the detected emission at the second wavelength is backscattered second harmonic generation.

19. The method of claim 15, wherein the real-time process control monitor further comprises an additional filter for selectively passing two-photon fluorescence emissions from the optical material transmitted through the objective lens to the detector, and further comprising monitoring two-photon fluorescence emissions from the optical material prior to writing the one or more scans to determine concentration of two-photon fluorescence emitter in the optical material.

* * * * *